(12) United States Patent
Frank et al.

(10) Patent No.: US 10,297,022 B2
(45) Date of Patent: May 21, 2019

(54) METHOD AND SYSTEM FOR ANALYSIS OF VOLUMETRIC DATA

(71) Applicant: THE REGENTS OF THE UNIVERSITY OF CALIFORNIA, Oakland, CA (US)

(72) Inventors: Lawrence R. Frank, San Diego, CA (US); Vitaly Galinsky, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 430 days.

(21) Appl. No.: 15/021,678

(22) PCT Filed: Sep. 15, 2014

(86) PCT No.: PCT/US2014/055712
§ 371 (c)(1),
(2) Date: Mar. 11, 2016

(87) PCT Pub. No.: WO2015/039054
PCT Pub. Date: Mar. 19, 2015

(65) Prior Publication Data
US 2016/0225146 A1 Aug. 4, 2016

Related U.S. Application Data

(60) Provisional application No. 61/877,866, filed on Sep. 13, 2013.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC ... G06T 7/0012; G06T 11/003; G06T 11/008; G06T 2200/04; G06T 2200/24;
(Continued)

(56) References Cited

U.S. PATENT DOCUMENTS 7,672,790 B2   3/2010   McGraw et al.
7,773,074 B2   8/2010   Arenson et al.
(Continued)

OTHER PUBLICATIONS

Assemlal et al. "Recent advances in diffusion MRI modeling: Angular and radial reconstruction", ELSEVIER, Medical Image Analysis 15 (2011) 369-396.*
(Continued)

*Primary Examiner* — Saif A Alhija
(74) *Attorney, Agent, or Firm* — Elanor Musick; Musick Davison, LLP

(57) ABSTRACT

A method is provided for modeling complex shapes from volumetric data utilizing spherical wave decomposition (SWD) by combining angular-only basis functions of the SPHARM with radial basis functions obtained by asymptotic expansion as a series of sine and cosine Fourier transforms to form the complete 3D basis. The 3D basis is used to expand the volumetric data. The resulting 3D volume representation allows construction of images of both surface and internal structures of the target object.

15 Claims, 13 Drawing Sheets

(51) Int. Cl.
| | |
|---|---|
| A61B 5/055 | (2006.01) |
| G01R 33/56 | (2006.01) |
| G06F 17/50 | (2006.01) |
| G06T 11/00 | (2006.01) |
| G01R 33/563 | (2006.01) |

(52) U.S. Cl.
CPC ..... *G01R 33/5608* (2013.01); *G06F 17/5009* (2013.01); *G06T 11/003* (2013.01); *G06T 11/008* (2013.01); *A61B 5/0044* (2013.01); *A61B 2576/023* (2013.01); *A61B 2576/026* (2013.01); *G01R 33/56341* (2013.01); *G06T 2200/04* (2013.01); *G06T 2200/24* (2013.01); *G06T 2207/10088* (2013.01); *G06T 2207/30016* (2013.01)

(58) Field of Classification Search
CPC ........... G06T 2207/10088; G06T 2207/30016; G06F 17/5009; A61B 5/0042; A61B 5/055; A61B 2576/023; A61B 5/0044; A61B 2576/026; G01R 33/5608; G01R 33/56341
USPC .......................................................... 703/1
See application file for complete search history.

(56) References Cited

U.S. PATENT DOCUMENTS

| | | |
|---|---|---|
| 8,742,754 B2 | 6/2014 | Hasan |
| 2005/0119834 A1 | 6/2005 | Kita et al. |
| 2005/0213809 A1 | 9/2005 | Lees et al. |
| 2008/0287796 A1 | 11/2008 | Kiraly et al. |
| 2011/0201935 A1 | 8/2011 | Collet-Billon et al. |
| 2011/0255763 A1 | 10/2011 | Bogoni et al. |

OTHER PUBLICATIONS

International Search Report/Written Opinion for PCT/US2014/055712, dated Dec. 8, 2014, 15 pages.
Behrens, T.E.J. et al., Probabilistic diffusion tractography with multiple fibre orientations: What can we gain?; NeuroImage vol. 34 (2007) pp. 144-155.
Bista, Sujal et al., Visualization of Brain Microstructure through Spherical Harmonics Illumination of High Fidelity Spatio-Angular Fields; IEEE Trans Vis Comput Graph, Dec. 2014; 20(12):2416-2525.
Burda, Z. et. al. , The various facets of random walk entropy, Presented at the 22nd Marian Smoluchowski Symposium on Statistical Physicics, Sakopane, Poland, Sep. 12-17, 2009.
Chung, Moo K. et al., Encoding cortical surface by spherical harmonics, Statistica Sinica vol. 18 (2008), 1269-1291.
Descoteaux, Maxime et al., Determilistic and probabilistic Q-Ball tractctography: from diffusion to sharp fiber distributions, No. 6273, Aug. 2007, Theme BIO, 36 pages.
Enrvik, Aron, 3D visualization of weather radar data, Thesis project in computer graphics at Linkoping University, Linkoping, Jan. 2002, LITH-ISY-EX-3252-2002, 92 pgs.
Frank, Lawrence R., et al., Information pathways in a discorded lattice, Physical Review, E89, 032142 (2014), 11 pgs.
Galinsky, Vitaly L. et al., Simultaneous multi-scale diffusion estimation and tractography guided by entropy spectrum pathways, IEEE Transactions on Medical Imaging, Dec. 2104, vol. 34, Issue 5, pp. 1177-1193.
Galinsky, Vitaly L. et al., Automated segmentation and shape characterization of volumetric data, NeroImage vol. 92 (2014) pp. 156-168.
Goncalves, Vitor, Interaction and visualization techniques for volumetric data of various scalar modalities: Integration of visualization and interaction, Electronica E. Telecomunicacoes, vol. 5, No. 3, Jun. 2011, pp. 344-351.
Huang, Heng, et al., Functional analysis of cardiac MR images using SPHARM modeling, Proc. SPIE 5747, Medical Imaging 2005: Image Processing, May 5, 2005, 1384; doi:10.1117/12.595954.
Lu, Meng, et al. Snake-based brain white matter fiber reconstruction, Bio-Medical Materials and Engineering vol. 24 (2014) pp. 2945-2953.
Mukherjee, P. et al., Diffusion tensor MR imaging and fiber tractography: technical considerations, AJNR Am J. Neuroradiol vol. 29, May 2009, pp. 843-852.
Mukherjee, P. et al., Diffusion tensor MR imaging and fiber tractography: theoretic underpinnings, AJNR Am J. Neuroradiol vol. 29, Apr. 2008, pp. 632-641.
Peters, J.F., et al., Classification of meteorological volumetric radar data using rough set methods, Pattern Recognition Letters, vol. 24 (2003) pp. 911-920.
Senjem, Matthew L., et al., Comparison of different methodological implementations of Voxel-based morphometry in neurodegenerative disease, Neuroimage vol. 26(2), Jun. 2005, pp. 600-608.
Shaw, Christopher D., et al., Real-time weather data on terrain, Proc. SPIE 4368, Visualization of Temporal and Spatial Data for Civilian and Defense Applications, Aug. 23, 2001, 8 pages.
Sinatra, Roberta, et al., Maximal-entropy random walks in complex networks with limited information, Physical Review vol. 83, 030103(R), 2011, 4 pages.
Styner, Martin, Statistical shape analysis of brain structures using SPHARM-PDM, Insight Journal, MICCAI 2006 Opensource Workshop, 7 pages.
Tournier, Jacques-Donald, et al., Diffusion tensor imaging and beyond, Magn Reson Med. vol. 65(6), Jun. 2011, pp. 1532-1556.

* cited by examiner

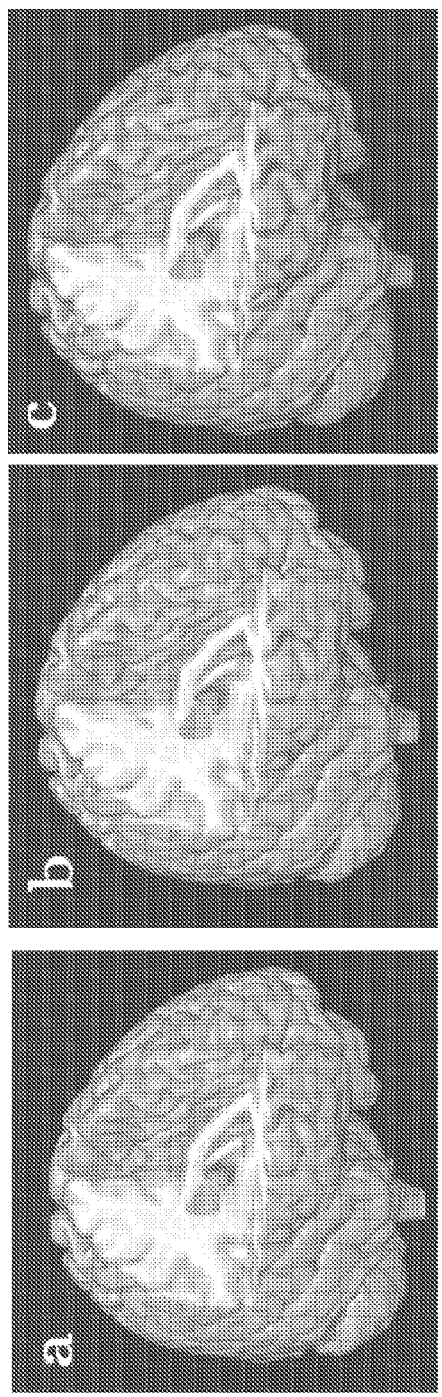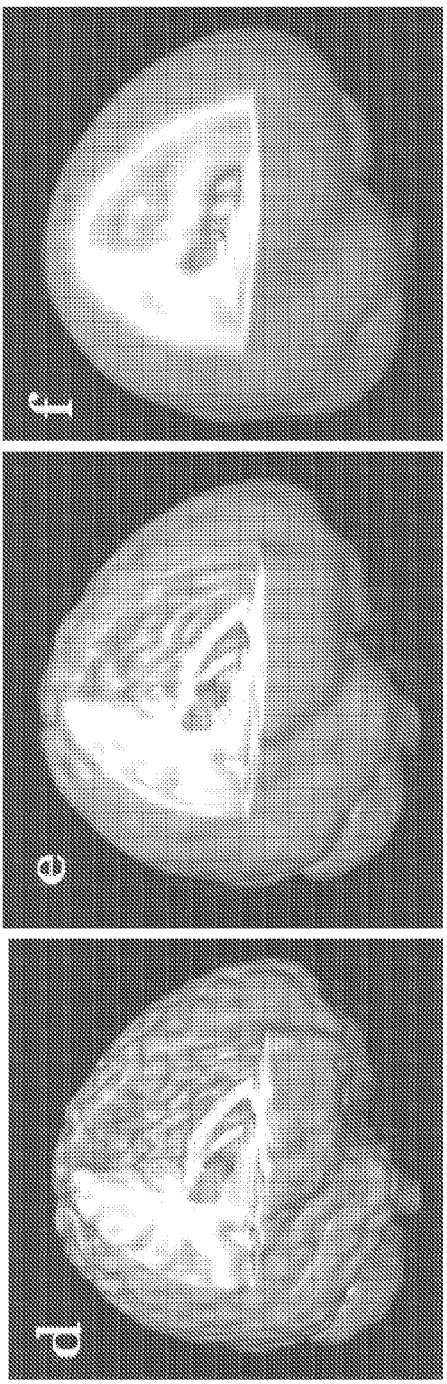

METHOD AND SYSTEM FOR ANALYSIS OF VOLUMETRIC DATA

RELATED APPLICATIONS

This application is a 371 national stage filing of International Application No. PCT/US2014/055712, filed Sep. 15, 2014, which claims the benefit of the priority of U.S. Provisional Application No. 61/877,866, filed Sep. 13, 2013.

GOVERNMENT RIGHTS

This invention was made with government support under grant No. NSF DBI-1147260 awarded by the National Science Foundation and grant No. MH096100 awarded by the National Institutes for Health. The government has certain rights in the invention.

FIELD OF THE INVENTION

The present invention relates to a method and system for characterization and modeling of complex three-dimensional shapes based on volumetric imaging data.

BACKGROUND OF THE INVENTION

In the field of medical imaging, various systems have been developed for generating medical images of various anatomical structures of individuals for the purpose of screening and evaluating medical conditions. These imaging systems include, for example, computed tomography (CT) imaging systems, magnetic resonance imaging (MRI) systems, X-ray systems, ultrasound systems, positron emission tomography (PET) systems, and single photon emission computed tomography (SPECT) systems, etc. Each imaging modality may provide unique advantages over other modalities for diagnosing and monitoring diseases, medical conditions or anatomical abnormalities. Three-dimensional modeling of image data has led to significant advances in both research and clinical capabilities.

A digital image consists of a two-dimensional (2D) array of data elements, pixels, that represent color or light intensity. Volumetric data are three-dimensional (3D) in structure, with a voxel as the smallest element. For example, computed tomography (CT) imaging systems can be used to acquire a volumetric dataset of cross-sectional images or two-dimensional (2D) "slices" that cover an anatomical part, allowing a 3D visualization of the part to be constructed.

Characterization of complex shapes embedded within volumetric data is an important step in a wide range of applications. Standard approaches to this problem employ surface based methods that require inefficient, time consuming, and error prone steps of surface segmentation and inflation to satisfy the uniqueness or stability of subsequent surface fitting algorithms. For example, the identification of structural changes in the brain on magnetic resonance imaging (MRI) scans is increasingly important in the study of neurological and psychiatric diseases. MRI can be used to identify and exclude treatable causes of cognitive impairment and it has also become important in the differential diagnosis of disease, in tracking disease progression, and for research purposes. Pathological changes in the brain resulting in cell loss manifest as loss of brain tissue, or atrophy, which can be detected by structural MRI. Characteristic patterns of atrophy are associated with specific neurodegenerative diseases. Traditional techniques of analyzing atrophy on MRI include visual assessment by experienced radiologists and manual measurements of structures of interest. However, automated techniques have been developed which allow the assessment of atrophy across large groups of subjects without the need for time-consuming manual measurements or subjective visual assessments.

Voxel-based morphometry (VBM) is one such automated technique that has grown in popularity since its introduction, largely because of the fact that it is relatively easy to use and has provided biologically plausible results. It uses statistics to identify differences in brain anatomy between groups of subjects, which in turn can be used to infer the presence of atrophy or, less commonly, tissue expansion in subjects with disease. The technique typically uses T1-weighted volumetric MRI scans and essentially performs statistical tests across all voxels in the image to identify volume differences between groups. For example, to identify differences in patterns of regional anatomy between groups of subjects, a series of t tests can be performed at every voxel in the image. Regression analyses can also be performed across voxels to assess neuroanatomical correlates of cognitive or behavioral deficits. The technique has been applied to a number of different disorders, including neurodegenerative diseases, e.g., Alzheimer's disease and dementia due to brain atrophy, movement disorders, epilepsy, multiple sclerosis, and schizophrenia, contributing to the understanding of how the brain changes in these disorders and how brain changes relate to characteristic clinical features. Although results from VBM studies are generally difficult to validate, studies have compared results of VBM analyses to manual and visual measurements of particular structures and have shown relatively good correspondence between the techniques, providing some confidence in the biological validity of VBM.

Standard approaches to volumetric data analysis employ surface based methods that require an initial segmentation of a surface and often a subsequent inflation of this surface to satisfy the uniqueness or stability of subsequent surface fitting algorithms. These methods are inefficient and time consuming because of the need for segmentation prior to fitting and the computationally intensive inflation process, the latter of which can be a significant source of errors due to creation of topological defects.

Continuing progress in the development of advanced imaging methods such as MRI and CT have facilitated the acquisition of high resolution, high contrast volumetric data that provides an approach for non-invasive yet highly informative assessment of brain morphology. The ability to utilize these valuable diagnostic and analytical tools in a cost effective manner is impeded by the massive quantity of data involved in modern volume images. This is particularly true of MRI data, which has a wide range of contrast mechanisms by which it can produce very high contrast of different types between complex soft tissues.

In concert with these advancements in imaging technologies, advances in computational methods, particularly in volume graphics and computer vision has resulted in tremendous increase in computational methods for morphology characterization and segmentation for comparative morphometry for both basic neuroscience studies on comparative brain anatomy and clinical studies of disease characterization and progression in humans, and for a broad range of studies in comparative biology.

In comparative biology, geometric morphometrics has emerged as an important tool for analysis, becoming commonly used to quantify morphology, wherein landmark points are identified in photographic (2D) images and then are fit to a warped mesh that provides a common coordinate system in which different specimens can be compared (Zelditch et al., 2004). These methods allow users to define key points of known morphological interest and statistically compare morphologies based on these points. However, the current predominant methods are based on 2D digital images or on 3D surfaces and are not readily applied to volumetric 3D data, such as those acquired by MRI or CT.

Recent advances in segmentation techniques were mostly originated from fuzzy logic and supervised and non-supervised clustering (Barra and Boire, 2000; Lin et al., 2012) both in 2D (Barra and Boire, 2001; Cocuzzo et al., 2011; Pedoia and Binaghi, 2012; Razlighi et al., 2012; Suri, 2001; Zavaljevski et al., 2000) and 3D (He et al., 2011; Kiebel et al., 2000; Klauschen et al., 2009; Popuri et al., 2012; Wels et al., 2011). Unfortunately, in spite of all advances none of these methods are able to provide truly robust and automated segmentation.

The most straightforward approach to segmentation is thresholding, which involves finding an intensity value, "the threshold", which distinguishes features of interest. This method is most frequently used to create a binary segmentation of an image, but it is also possible to distinguish three or more intensity classes using multithresholding (Zavaljevski et al., 2000). Thresholding works particularly well with imaging modalities such as CT data where images are often essentially binary between bone (bright) and soft tissue (very dark) and segmentation can be practically automated. Automated methods for MRI data, however, are exceedingly difficult because of adjoining regions with similar values (i.e. low contrast), partial voluming (multiple tissue types within a single voxel), image noise, and intensity inhomogeneities, all of which are common to MR images (Atkins and Mackiewich, 2000; Pham et al., 2000).

Region growing methods extract connected regions in images based on criteria that can include both intensity and edges. These methods are susceptible to noise, which can create artificial divisions between connected regions, and partial volume effects, which can merge disconnected regions. These effects can be reduced by limiting growth to topology-preserving deformations (Mangin et al., 1995), but user input is still required to select seed regions. Clustering algorithms alternate between segmenting the image and characterizing the properties of each segmented class, iterating until a stopping criterion is reached (Barra and Boire, 2000, 2002; Liang et al., 1994; Pachai et al., 2001; Popuri et al., 2012). Clustering is generally susceptible to both noise and image inhomogeneities, though robustness to intensity inhomogeneities has been demonstrated (Pham and Prince, 1999). Given a Bayesian prior model, Markov random field models can be incorporated in clustering methods to minimize susceptibility to noise (Li, 1994).

Atlas-guided approaches provide an option that may be feasible (Klein et al., 2009). In such methods, a linear or non-linear transformation is found mapping the pre-segmented atlas image to the target image. This changes the tissue classification problem to a registration or deformation problem. However, to effectively use atlas-guided methods, very large and detailed databases, or atlases of reference objects, are needed. This puts the onus of the quantitation on an accurate and reproducible method for atlas creation.

One important and rather successful direction in brain quantifying and characterization has emerged from analyses of parameterization of surfaces for 3D shape description using spherical harmonics (SPHARM) representation (Brechbühler et al., 1995; Kazhdan et al., 2003). SPHARM is a technique for parameterizing anatomical boundaries using the spherical harmonic basis. The surface coordinates are expressed as a linear combination of basis functions. SPHARM can be used to construct the Fourier series expansion of a functional measurement. Shape signatures can be created using the SPHARM decomposition at several concentric spheres or at a single surface that represents a highly convoluted geometry of the cerebral cortex. Two steps are involved in converting the object surface to its SPHARM shape description: surface parameterization and expansion into a complete set of SPHARM basis functions. In the SPHARM method, any function $f$ is assumed to be defined on a sphere, $f(\theta, \phi)$, and decomposed as the sum of its spherical harmonics:

$$f(\theta, \phi) = \sum_{l=0}^{\infty} \sum_{m=-l}^{l} f_{lm} Y_l^m(\theta, \phi) \quad (1)$$

where $Y_l^m$ is the spherical harmonic of degree l and order m, with low values of l corresponding to lower frequency information. The Fourier coefficients $f_{lm}$, are used to reconstruct the object surface, with a greater number of coefficients providing a more detailed construction. Since $L_2$-norms of spherical functions are not affected by rotations, a rotationally-invariant shape signature may be given as $SH(f) = \{\|f_0(\theta,\phi)\|, \|f_1(\theta,\phi)\|, \ldots\}$, where $f_l(\theta, \phi) = \sum_{m=-l}^{l} f_{lm} Y_l^m(\theta, \phi)$ are the frequency components of $f$. An alternate signature can be calculated more quickly and directly from the coefficients, defining $SH(f) = \{A_0, A_1, \ldots\}$, where the $A_l$ are $L_2$-norms of all the coefficients $f_{lm}$ at each l: $A_l = \sum_{m=-l}^{l} |f_{lm}|^2$. The spherical harmonics $Y_l^m$ are continuous functions, but for computational applications, $f$ is only sampled at $N_\Omega$ discrete angles. To create a shape signature for a 3D object, the shape is sampled at $N_\Omega$ angles and $N_y$ radii, SH is calculated at each radius up to $l = L_{max}$, and the result is represented as a 2D grid of size $L_{max} \times N_y$.

The SPHARM application described by Kazhdan et al. (2003) provided more general shape classification using clean data (e.g., a set of 1,890 household objects), but in noisy MRI data, the SPHARM deals with noise automatically, since the noise does not appear in the lower frequencies that dominate shape descriptions. Many internal structures remain visible in data reconstructed from the signatures, while the signatures themselves require significantly less storage space than the original data. This general method was improved further by appropriate filtering (i.e. using exponentially weighted Fourier or spherical harmonics series, Chung et al. 2008a, 2007, 2008b). The weighting reduces a substantial amount of the so called ringing (or Gibbs) phenomenon and aliasing (or Moire) patterns (Gelb, 1997)), both appearing because of relatively slow convergence of Fourier series when used for representing discontinuous or rapidly changing measurements.

Overall, these modifications of the SPHARM method with filtering or exponential weighting (Chung et al., 2008a, 2007, 2008b) allowed successful parameterization of the cortical surface including characterization of the local difference in gray matter concentration. Nevertheless, techniques based on the SPHARM morphometry method—tensor-based morphometry—uses the cortical surface already segmented out of noisy MRI data and quantifies the amount of gray matter only in a narrow layer along the tangential direction of the surface via the concept of a local area element. Hence, the analysis cannot be directly used for volumetric MRI data.

An extension of spherical harmonics decomposition that naturally allows incorporation of complete 3D volume data is known in various areas of physics, e.g., in quantum physics for description of waveform solutions of the Schrödinger equation (Gersten, 1971), in atomic and nuclear physics for approximation of Coulomb scattering function (Barnett, 1996, 1981)), and in astrophysics for analyses of anisotropies of microwave background, as well as for quantum gravity (Abbott and Schaefer, 1986; Binney and Quinn, 1991; Leistedt et al., 2012). However, such approaches have not previously been utilized for characterization and modeling of volumetric data.

SUMMARY OF THE INVENTION

Methods are provided for the characterization of complex shapes embedded within volumetric data using spherical wave decomposition (SWD) of the data to directly analyze the entire data volume. This obviates the segmentation, inflation, and surface fitting steps, significantly reducing the computational time and eliminating topological errors while providing a more detailed quantitative description based upon a more complete theoretical framework of volumetric data.

Advanced computational methods are provided for accurate quantitative characterization and comparison of specimen morphology from high resolution 3D voxel-based digital imaging modalities. With the growing recognition of the importance of digital libraries of biological specimens derived from advanced imaging methods, such as the NSF funded Digital Fish Library (DFL) and Digital Morphology (DigiMorph) projects, advanced methods for utilizing these data are of great importance, but pose significant technical challenges. Two broad classes of problems are of critical importance: 1) the ability to quantitatively characterize complicated morphological features from high resolution volumetric data and 2) methods for comparing such features between specimens. Our objective is to develop two specific computational methods for geometric morphological analysis that can optimally characterize and compare geometric features embedded within real 3D imaging data, and are robust to noise and resolution limitations:

The present method for modeling complex shapes utilizes spherical wave decomposition (SWD), combining angular-only basis functions of the SPHARM with spherical Bessel functions as the radial basis functions, forming the complete 3D basis. This basis is appropriate for expanding any function $f(r, \theta, \varphi)$ defined inside a sphere of radius $\alpha$. The expansion coefficients have the advantage of allowing characterization of the internal structure simultaneously with the overall shape. Because they are not surface-based, there is no need to address topological discrepancies or to first perform surface based segmentation. Thus, the inventive approach offers a more complete description of noisy volumetric data and is also more computationally efficient.

The methods can be used on a wide range of multidimensional volumetric data such as magnetic resonance imaging data of the human brain for morphological characterization or diffusion tensor magnetic resonance imaging for characterization of neuronal fibers and brain connectivity. Additional applications include anatomical mapping and quantification of changes in human anatomy, including brain changes during diseased states, which may be useful in clinical studies. Generally, any field that generates models using volumetric data can benefit from the inventive approach. For example, further implementations of the inventive method may include 3D visualization of weather data, e.g., Doppler radar, for detection and prediction, and geotechnical assessments of oil, gas or mineral deposits and geodynamic simulations using particle-grid based methods.

The methods described herein may be embodied on a computer program product which is executed on a computer with a processor and a memory to compute the SWD and determine the complex shapes.

In one aspect of the invention, a method for generating a three-dimensional model of a structure, comprises: inputting into a computer processor volumetric data comprising 3-dimensional data points comprising Cartesian coordinates; transforming the volumetric data into spherical coordinates comprising radial and angular variables; expanding the transformed spherical coordinates into 3D basis functions by expanding angular variables into spherical harmonic basis functions to determine angular coefficients and expanding the radial variables into radial basis functions to determine radial coefficients; combining angular coefficients and radial coefficients to construct a 3D volume representation of the structure; transforming the 3D volume representation of the structure into Cartesian coordinates; and displaying the transformed 3D volume representation of the structure on a graphical user interface. In some embodiments, the radial basis functions are spherical Bessel functions. The volumetric data may be MRI images data so that the displayed 3D volume representation is brain morphology.

In another aspect of the invention, a method for modeling a target object using input volumetric data, comprises: combining angular-only basis functions of SPHARM with spherical Bessel functions as the radial basis functions to form a complete 3D basis; expanding the input volumetric data using the complete 3D basis; and generating an output comprising displaying a 3D volume representation of the target object.

BRIEF DESCRIPTION OF THE DRAWINGS

FIGS. 1a-1f illustrate a series of images of three-dimensional (3D) brain reconstructions obtained with different degrees of spherical wave decomposition (SWD).

FIG. 6 illustrates images of gray matter two-dimensional (2D) slices (panels a-c) and 3D view (panel d) segmented out from the full 3D brain of FIG. 1a.

FIG. 7 illustrates white matter 2D slices (panels a-c) and 3D view (panel d) segmented out from the full 3D brain in FIG. 1a.

FIGS. 9a and 9b show the results of FreeSurfer, processing, and FIGS. 9c and 9d shows the results of SPHARM+FreeSurfer, all overlaid on the grey scale images of the original volumetric data. FIGS. 9e and 9f show corresponding slices of the white matter volume obtained by the SWD.

DETAILED DESCRIPTION

Figures 2A, 2B, 2C:
FIGS. 2a-2f illustrate the same series of 3D brain reconstructions of FIGS. 1a-1f after the application of Weighted Fourier Smoothing (WFS).
Figures 2D, 2E, 2F:

The present method for modeling complex shapes utilizes spherical wave decomposition (SWD), combining angular-only basis functions of the SPHARM with spherical Bessel functions as the radial basis functions, forming the complete 3D basis. This basis is appropriate for expanding any function $f(r, \theta, \varphi)$ defined inside a sphere of radius $\alpha$. The expansion coefficients have the advantage of allowing characterization of the internal structure simultaneously with the overall shape. Because they are not surface-based, there is no need to address topological discrepancies or to first perform surface based segmentation. Thus, the inventive approach offers a more complete description of noisy volumetric data and is also more computationally efficient.

The basis functions for the spherical wave decomposition are composed of radial and angular parts. They can be obtained as eigensolutions of Laplace equation (or particular solution of Helmholtz's equation) $\nabla^2 f + k^2 f = 0$ (Lebedev, 1972), where the Laplacian $\nabla^2$ is expressed in spherical coordinates as $$\nabla^2 = \nabla_r^2 + \frac{1}{r^2}\nabla_\Omega^2 \qquad (2)$$

$$= \frac{1}{r^2}\frac{\partial}{\partial r}\left(r^2 \frac{\partial}{\partial r}\right) + \frac{1}{r^2 \sin\theta}\frac{\partial}{\partial \theta}\left(\sin\theta \frac{\partial}{\partial \theta}\right) + \frac{1}{r^2 \sin\theta}\frac{\partial^2}{\partial \phi^2}.$$

For a function $f(r, \theta, \varphi)$ defined inside a solid sphere of radius $r \leq \alpha$, the following expansion, obtained by separation of variables, is valid $$f(r, \theta, \phi) = \sum_{n=1}^{\infty}\sum_{l=0}^{\infty}\sum_{m=-l}^{l} f_{lmn} R_{ln}(r) Y_l^m(\theta, \phi). \qquad (3)$$

where the angular dependency is contained in the spherical harmonics $Y_l^m(\theta, \phi)$—the eigensolution of the angular part of the Laplacian with the eigenvalues $\lambda_l = -l(l+1)$:

$$\nabla_\Omega^2 Y_l^m = \lambda_l Y_l^m. \qquad (4)$$

The spherical harmonic $Y_l^m$ of degree l and order m allows separation of the $\theta$ and $\varphi$ variables when expressed using associated Legendre polynomials $P_l^m$ of order m as $$Y_l^m(\theta,\phi) = c_{l,m} P_l^m(\cos\theta) e^{-im\phi}, \qquad (5)$$

where $c_{l,m}$ is the normalization constant $$c_{l,m} = \sqrt{\frac{2l-1(l-m)!}{4\pi(l+m)!}},$$

which is selected to guarantee the orthonormality condition
$\int_0^\pi \int_0^{2\pi} Y_l^m Y_{l'}^{m'} \sin\theta d\theta d\phi = \delta_{ll'}\delta_{mm'}$.

The radial component $R_{ln}(r)$ of Equation (3) is obtained as the eigenfunction of the radial Laplacian $$\nabla_r^2 R_{ln} = -\left(k^2 + \frac{\lambda_l}{r^2}\right) R_{ln}, \qquad (6)$$

and can be expressed through the spherical Bessel function as $$R_{ln}(r) = \frac{1}{\sqrt{N_{ln}}} j_l(k_{ln} r), \qquad (7)$$

The normalization constants $N_{ln}$ as well as the discrete spectrum wave numbers $k_{ln}$ are determined by the choice of boundary conditions. For Dirichlet boundary condition, i.e., $f(r, \theta, \phi) = 0$ for $r \geq \alpha$, they can be expressed as $$N_{ln} = \frac{a^3}{2} j_{l+1}^2(x_{ln}), \quad k_{ln} = \frac{x_{ln}}{a}, \qquad (8)$$

where $\{x_{ln}\}$ are ordered for $n \geq 1$ zeroes of spherical Bessel function $j_l(x)$. With this choice of the discrete spectral numbers $k_{ln}$ and the normalization constants $N_{ln}$, the orthonormality conditions for $R_{ln}(r)$ reads
$\int_0^a R_{ln} R_{ln'} r^2 dr = \delta_{nn'}$, Using the basis function, $R_{nl}(r) Y_l^m(\theta, \phi)$ the spherical Fourier coefficients $f_{lmn}$ can be obtained as
$f_{lmn} = \int_0^a \int_0^\pi \int_0^{2\pi} f(r,\theta,\phi) R_{nl}(r) Y_l^m(\theta,\phi) r^2 dr \sin\theta d\theta d\phi.$ (9)

As in SPHARM, a rotationally-invariant signature can be calculated directly from the coefficients $f_{lmn}$ by taking the $L_2$-norm of all the $f_{lmn}$ each l and n:

$$S_{ln} = \sum_{m=-l}^{l} |f_{lmn}|^2. \qquad (10)$$

The resulting signature, represented again as a 2D grid, now of size $L_{max} \times N_{max}$, where $N_{max}$ is the number of spherical Bessel functions used in radial expansion, is purely in frequency space.

Straightforward calculations of the multiple radial shell SPHARM decomposition require $O(N_r N_\Omega L_{max}^2)$ operations. For calculation of volumetric SWD spectra, a separation of variables between the angular and the radial parts can be used. Still the brute force calculation of integrals in Equation (9) results in even higher computational toll for the SWD than in the SPHARM—$O(N_r N_\Omega L_{max}^2 N_{max})$.

Fortunately, when taken independently, both the angular and the radial parts allow use of fast $O(N \log N)$ transforms. The angular spherical harmonics decomposition was implemented using a divide and conquer approach and a fast Legendre transform (Driscoll and Healy, 1994; Healy et al., 1996, 2004; Mohlenkamp, 1999; Rokhlin and Tygert, 2006). For the radial spherical Bessel transform evaluation, several different fast implementations are also available (Bisseling and Kosloff, 1985; Koval and Talman, 2010; Pettitt et al., 1993; Sharafeddin et al., 1992; Talman, 1978, 2009; Toyoda and Ozaki, 2010). In the present implementation, the approach used by Toyoda and Ozaki (2010) was followed after replacing their recurrence formula with asymptotic expansion of the integral according to the following procedure.

The integral representation of the spherical Bessel function is given by $$j_l(z) = \frac{1}{2i^l}\int_{-1}^{1} e^{izt} P_l(t) dt, \quad (11)$$

where $P_l(t)$ is the Legendre polynomials. By substituting Equation (11) into the radial part of the SWD transform $$f(k,\theta,\phi) = \int_0^\infty jl(kr) f(r,\theta,\phi) r^2 dr, \quad (12)$$

and integrating by parts, the transform can be rewritten as follows:

$$f(k, \theta, \phi) = \frac{1}{2i^l}\int_{-1}^{1} dt P_l(t) \int_0^\infty r^2 dr e^{ikrt} f(r, \theta, \phi) \quad (13)$$

$$= \frac{1}{2i^l}\int_{-1}^{1} dt P_l(t) \frac{1}{ik}\frac{d}{dt}\int_0^\infty r dr e^{ikrt} f(r, \theta, \phi)$$

$$= \frac{1}{2i^l}\left[\frac{1}{ik} P_l(t)\int_0^\infty r dr e^{ikrt} f(r, \theta, \phi)\Big|_{-1}^{1} - \frac{1}{ik}\int_{-1}^{1} dt P'_l(t)\int_0^\infty r dr e^{ikrt} f(r, \theta, \phi)\right]$$

$$= \frac{1}{2i^l}\left[\sum_{n=0}^{N}\frac{(-1)^n}{(ik)^{n+1}} P_l^{(n)}(t)\int_0^\infty r^{1-n} dr e^{ikrt} f(r, \theta, \phi)\Big|_{-1}^{1} - \frac{(-1)^N}{(ik)^{N+1}}\int_{-1}^{1} dt P_l^{(N+1)}(t)\int_0^\infty r^{1-N} dr e^{ikrt} f(r, \theta, \phi)\right].$$

As derivative $P_l^{(N)}(t)$ vanishes for N>l, the summation in Equation 13 only goes to N=l, so that $$f(k, \theta, \phi) = \frac{1}{2i^l}\sum_{n=0}^{l}\frac{(-1)^n}{(ik)^{n+1}} P_l^{(n)}(t)\int_0^\infty r^{1-n} dr e^{ikrt} f(r, \theta, \phi)\Big|_{-1}^{1}. \quad (14)$$

The integrals in Equation (14) evaluated at t=±1 represent the one-dimensional half plane Fourier transforms of $f(r, \theta, \phi)$ multiplied by various powers of r. Using the parity property of the Legendre polynomials $P_l^{(n)}(-t) = (-1)^{l+n} P_l^{(n)}(t)$ the Fourier integrals in Equation (14) can be rewritten through the standard sine and cosine Fourier series instead:

$$f(k, \theta, \phi) = \sum_{n=0}^{l}\frac{P_l^{(n)}(1)}{k^{n+1}} \times \quad (15)$$

$$\begin{cases}(-1)^{\lfloor\frac{l-n}{2}\rfloor}\int_0^\infty r^{1-n} dr \sin(kr) f(r, \theta, \phi), & l+n \text{ is even} \\ (-1)^{\lfloor\frac{l-n+1}{2}\rfloor}\int_0^\infty r^{1-n} dr \cos(kr) f(r, \theta, \phi), & l+n \text{ is odd}\end{cases}$$

where $\lfloor x \rfloor$ denotes floor(x), i.e., the largest integer that does not exceed x.

From Equation 15, it can be seen that all the coefficients of the spherical Bessel transform can be obtained by rearrangement of coefficients of sine and cosine Fourier transforms of $f(r, \theta, \phi)$ multiplied by powers of radius $r^e$ with integer exponent e decreasing from 1 to l−1.

However, for the purpose of efficient numerical implementation it is not necessary to compute all the terms in summation of Equation (15). Instead, a low upper limit of summation (N=0 or 1) can be used and the residual (the last term in Equation (13) can be evaluated using numerical integration, progressively evaluating the terms until they are smaller than some prescribed threshold. Because the Fourier expansion decreases not slower than $k^{-1}$ (even for discontinuous functions) and taking into account an additional multiplication by a factor $1/k^{N+1}$, this seems to be always possible even despite the presence of large derivative of the Legendre polynomials $P_l^{(N+1)}$.

Volumetric MRI data are usually obtained on a Cartesian 3D grid. At the same time, in order to be able to use the fast transforms, both angular and radial parts should be defined on spherical grids with special grid placements. Therefore, the first step of a forward transform (i.e., transform to the frequency domain) and the last step of a backward transform (from the frequency domain) should provide a way of resampling the input and output 3D volume data from or to a Cartesian grid, i.e., the following convolutions should be computed $$f(r) = \iiint \Im_x(x-x') f(x') d^3x',$$

$$f(x) = \iiint \Im_r(r-r') f(r') dV',$$

where x=(x, y, z) and r=(r, θ, φ) are related through the change of variables from Cartesian to spherical system of coordinates, x=r sin θ cos φ, y=r sin θ sin φ, z=cos θ, with the volume element $dV=r^2 dr \sin\theta d\theta d\phi$. Selection of different resampling filters $\Im_x$ and $\Im_r$ (from simple nearest neighbor to complex multipoint interpolation) provides means for balancing between speed and quality.

Example 1: Brain Morphology from MRI Data

The SWD method was tested on high resolution MRI anatomical data of a normal human brain collected an a GE 3T MR750 Clinical Scanner using an inversion recovert T1-weighted 3D fast spoiled gradient recalled echo pulse sequence with parameters: flip angle α=12°, echo time TE=3 ms, repetition time TR=8 ms, matrix size=(RL, AP, IS)= (172×256×256), field of view FOV=(170×240×240) mm for a resolution of (1×0.938×0.938) mm. Characterization of this data as a function of SWD degrees $L_{max}$ and $N_{max}$ is shown in FIGS. 1a-1f for progressively lower degrees of SWD transform. The largest degree ($L_{max}=N_{max}=300$, shown in FIG. 1b) to exceed the physical dimensions of the original brain (FIG. 1a) confirms that a high degree SWD is capable of reconstructing all details of the original dataset and produce a visually indistinguishable result. It also demonstrates that the SWD approach is capable of handling a large volume of frequency domain data (>300³ modes). Significant reduction in the degrees of SWD transform to $L_{max}=N_{max}=100$ (FIG. 1c), also produces a virtually indistinguishable brain. Even a relatively low resolution $L_{max}=N_{max}=50$ shown in FIG. 1d, with roughly a hundred times less information content than in the original volume, is able to reproduce both external and internal structure of the original brain.

Finally, the last two low resolution reconstructions, seen in FIGS. 1e and 1f (with degrees equal to 25 and 10, respectively) show the expected significant smoothing of both external and internal details. But even the lowest degree result, which uses less than 1/104 of the original data, is able to capture and reproduce some important low resolution features of the original brain. To illustrate the computational effectiveness of the inventive SWD implementation, Table 1 provides the computational timing for various stages of the implementation of inventive SWD method for different degrees $\{L_{max}=N_{max}\}$ of transform. These timings were obtained for the same brain dataset using single thread INTEL® Core™ i7-2760QM CPU 2.40 GHz.

Simple nearest neighbor interpolation has been used for interpolation to Cartesian domain for all results shown in Table 1 (last column $\tilde{\mathfrak{I}}_r:r\Rightarrow x$) as well as for all transform degrees reported in FIGS. 1a-1f. For interpolation to spherical domain ($\tilde{\mathfrak{I}}_x:x\Rightarrow r$) averaging was used over all the neighbors in the box obtained by mapping local spherical unit volume to Cartesian coordinates.

TABLE 1

| Order $L_{max}$ | $\tilde{\mathfrak{I}}_x: x\Rightarrow r$ | $f(r)\Rightarrow f_{lmn}$ | $f_{lmn}\Rightarrow f(r)$ | $\tilde{\mathfrak{I}}_r: r\Rightarrow x$ |
|---|---|---|---|---|
| 400 | 338.8 | 56.26 | 51.95 | 2.65 |
| 300 | 143.6 | 20.01 | 19.22 | 2.42 |
| 200 | 43.97 | 4.68 | 4.99 | 2.17 |
| 100 | 5.53 | 0.45 | 0.46 | 1.82 |
| 50 | 0.71 | 0.05 | 0.05 | 1.61 |

Timings (sec) shown in columns above.

It is important to note that the rows in Table 1 do not necessarily correspond to the work-flow of the SWD method. For example, it is possible to produce spherical interpolation using one resolution, then generate frequencies using a different degree, transform them back with yet another degree of transform, and finally arrive at Cartesian volumetric data with a different resolution. Hence, Table 1 is provided to illustrate scaling of various parts of the SWD computation with a change of the degree of transform. The most computationally demanding part of the method is the interpolation to spherical coordinates ($\tilde{\mathfrak{I}}_x:x\Rightarrow r$) that uses box averaging of neighbors. It took roughly 5.5 minutes to produce the largest $400^3$ resolution in spherical domain. However, it should be noted that double the reported resolution is used for all internal calculations. Thus, in this case, the actual resolution was $800^3$, that is 8 times larger. But a change of the execution time with a change of the degree $L_{max}$ follows $O(L_{max}^3)$ pattern, i.e., it scales linearly with the total number of grid points processed. Overall, the performance of the SWD method looks very competitive in comparison with the SPHARM, taking only on the order of seconds for $L_{max}=N_{max}\sim100$, that is for calculation of all $L_{max}\times N_{max}/2$ spectral coefficients. In contrast, single surface calculations of all the coefficients of SPHARM up to degree $L_{max}=78$—that is $L_{max}/2$ total coefficients—takes more than few hours for direct numerical evaluation of integrals, and more than 5 minutes for the iterative residual fitting (IRF) algorithm of Chung et al. (2008a, 2007, 2008b).

The performance boost provided by the SWD approach relative to the fastest SPHARM implementation was not obtained at the expense of accuracy. On the contrary, analysis of root-mean-square (RMS) errors presented in the next section clearly shows that the SWD consistently produces several times lower RMS errors then the SPHARM in the same range of parameters. This means that the volume decomposition using complimentary radial and angular basis is clearly superior in term of accuracy to the angular only SPHARM decomposition.

To include smoothing effects (in addition to smoothing that can be provided by appropriate choice of resampling filters $\tilde{\mathfrak{I}}_x$ and $\tilde{\mathfrak{I}}_r$ the weighted Fourier series (WFS) was also added into the representation in the spherical wave decomposition (Chung et al., 2007) by the inclusion of exponential weighting factors exp $(\lambda_l t)$ in the original series (3):

$$f(r_i) = \sum_{n=1}^{\infty}\sum_{l=0}^{\infty}\sum_{m=-l}^{l} e^{\lambda_l t} f_{lmn} R_{ln}(r_i) Y_l^m(\theta_i, \phi_i), \quad (16)$$

where and $\lambda_l=-l(l+1)$ is a parameter that may be used to control the bandwidth. The results of the SWD with WFS are shown in FIGS. 2a-2f for t=0.0001 (FIG. 2b), 0.0005 (FIG. 2c), 0.001 (FIG. 2d), 0.005 (FIG. 2e), and 0.01 (FIG. 2f) as well as for no smoothing with t=0 (FIG. 2a). By comparing these images with FIGS. 1a-1f, it can be seen that the WFS smoothing with 0.01>t>0.001 from the visual standpoint resembles limiting the degree of SWD transform to somewhere below $L_{max}=50$ level, whereas values of 0.001>t>0.0001 correspond to $L_{max}$ values between 50 and 100.

Figure 3B:
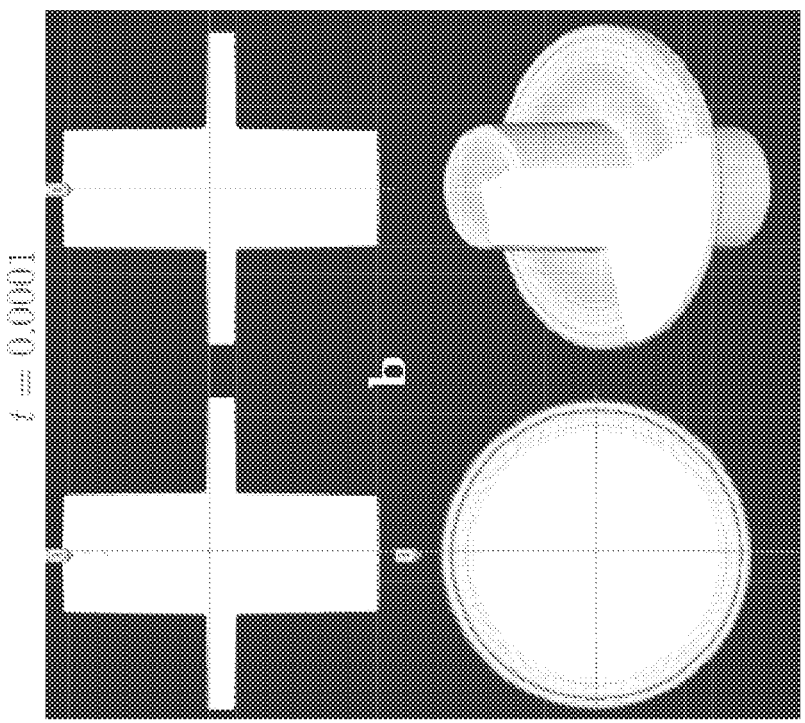
FIGS. 3a and 3b illustrate SWD representations of a discontinuous (3D step function) shape without WFS and with WFS, respectively.
Figure 3A:
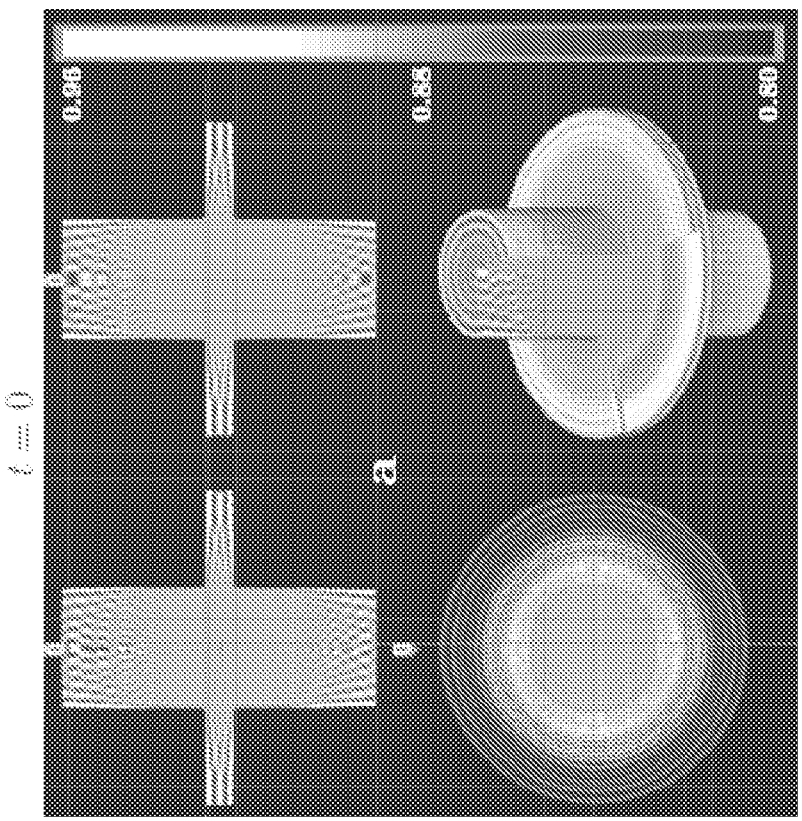

To illustrate that the inclusion of WFS reduces the substantial amount of the Gibbs phenomenon—ringing artifacts associated with the slow convergence of a Fourier series (Gelb, 1997)—the SWD was applied both with and without the WFS to a slowly converging SWD representation of a 3-D step-like function (FIGS. 3a and 3b). For comparison with Chung et al. (2008a) the same set of parameters was used for the degree ($L_{max}=N_{max}=78$) and the bandwidth (t=0.0001) of the SWD transform. The weighted SWD shown in FIG. 3b clearly demonstrates fewer ringing artifacts than the original SWD of FIG. 3a, however, the reduction is not as profound as in the weighted SPHARM of the same degree and bandwidth, probably due to higher overall accuracy of the SWD approach and additional smoothing provided by the resampling filters $\tilde{\mathfrak{I}}_x$ and $\tilde{\mathfrak{I}}_r$.

Analysis of quantitative procedure of finding optimal degree of SWD transform that is characteristics of some particular level of smoothing is provided in the next section.

Example 2: Selection of Optimal Order of SWD Transform

To estimate how well the SWD with some preselected degrees $L_{max}$ and $N_{max}$ will represent any particular dataset the root mean square deviation can be used. Because increasing the angular $L_{max}$ and the radial $N_{max}$ degrees of SWD increases not only the goodness-of-fit, but also the number of coefficients to be estimated, finding the optimal degree where this increase in the number of parameters is warranted by the goodness-of-fit is very important. This is even more important for the SWD than in the single surface SPHARM approach (Chung et al., 2008a, 2007, 2008b), as the growth of coefficients occurs cubically, not quadratically.

Although in the SWD the angular and the radial degrees can be changed independently, the number of zeros of the spherical Bessel function that fall inside the sphere of radius a corresponds to the number of zeros in latitudinal or longitudinal directions when $L_{max}\sim N_{max}$. Hence, for a purpose of finding the optimal degree order, one can assume that $N_{max}=L_{max}$.

Following Chung et al. (2007), assume that distribution of the Fourier coefficients $f_{lmn}$ can be approximated to follow normal distribution $N(\mu_{lmn}, \sigma_l^2)$ with equal variance $\sigma_l$ within the same degree. This corresponds to the following k−1 degree model $$f_{k-1}(r_i) = \sum_{n=1}^{k-1}\sum_{l=0}^{k-1}\sum_{m=-l}^{l} e^{-l(l+1)t}\mu_{lmn}R_{ln}(r_i)Y_l^m(\theta_i, \phi_i) + \epsilon(r_i) \quad (17)$$

where $\epsilon$ is a zero mean isotropic Gaussian random field. One can then test if increasing the degree of the model above k−1 is statistically significant by testing the null hypothesis $$H_0: \mu_{lmn}=0 \text{ for } l=k, n=k, |m|\leq k, \quad (18)$$

For the construction of test statistic, the residual sum of squares (RSS) was used for the (k—1) degree model $f_{k-1}$, that is $$RSS_{k-1} = RSS(f_{k-1}) = \sum_{i=1}^{N}(f(r_i) - f_{k-1}(r_i))^2. \quad (19)$$

Figure 4:
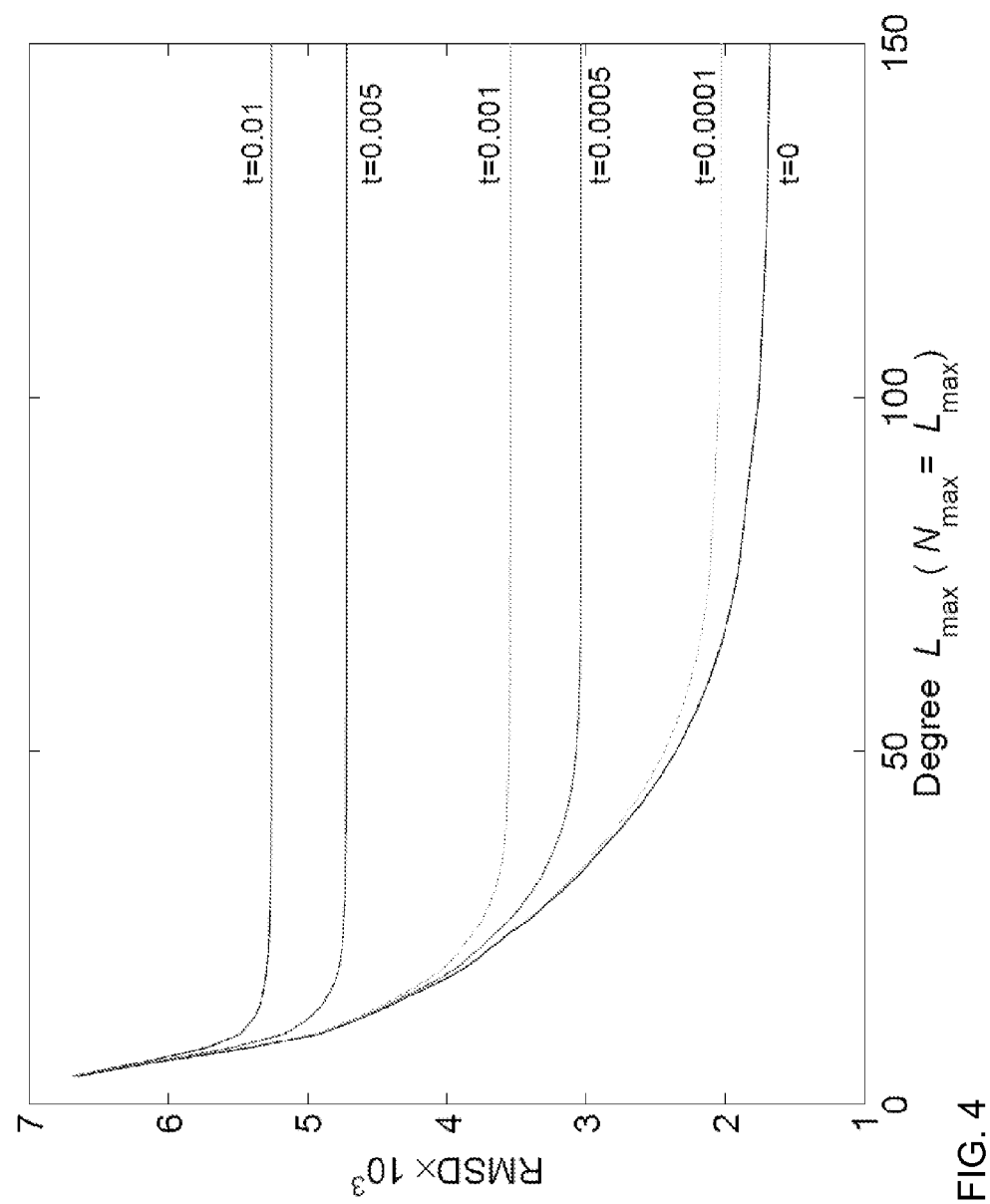
FIG. 4 illustrates a plot of root-mean-square-deviation (RMSD) for each of 6 volumes shown in FIG. 2 as a function of the SWD degree.

FIG. 4 is a plot of the root-mean-square-deviation ($RMSD_k=\sqrt{RSS_k/N}$) as a function of k (which is the SWD degree $L_{max}=N_{max}$) for the six brain reconstructions shown in FIGS. 2a-2f obtained for different values of exponential smoothing parameter t. (The corresponding values of t are printed for each curve.) The overall behavior seems consistent with the SPHARM, showing that initial fast decrease of the root mean square deviation gradually slows down and flattens out. The value of error in the flat region as well as the degree where the transition to the flat region occurs depends on the smoothing parameter t, also consistent with the SPHARM. The important difference of the SWD is that it consistently shows several times lower RMS errors then the SPHARM in the same range of $L_{max}$ and t parameters. This leads to the reasonable conclusion that volume decomposition using complimentary radial and angular basis is superior in terms of accuracy to single surface only (or even the shell of surfaces) angular SPHARM decomposition.

The test statistic used in SPHARM was modified to account for the different numbers of "groups" and "observations" used in each of the methods:

$$F = \frac{(RSS_{k-1} - RSS_k)/(3k^2+k)}{RSS_{k-1}/(N-(k+1)^2k)} \sim F_{3k^2+k, N-(k+1)^2k}, \quad (20)$$

The resulting distribution is again the F-distribution, with different values of the degrees-of-freedom $(3k+1)k$ and $N-k(k+1)^2$. The optimal SWD-degree can be obtained by computing the F statistic for each degree k up to the point when the corresponding P-value becomes bigger than the pre-specified significance $\alpha$. The results for $\alpha=0.01$ are comparable to the SPHARM values, i.e., for the bandwidth t=0.0001 the optimal SWD degree has been determined to be k=80 vs k=78 for the SPHARM approach.

Example 3: Use of SWD for Volume Segmentation

An important difference between the SWD and the SPHARM methods lies in the possibility of a relatively simple and straightforward modification of the SWD to naturally and effectively handle the highly complex task of volume segmentation. Segmentation is not tractable by the SPHARM method itself because it requires processing of the entire volumetric data but SPHARM is based on a partial decomposition valid only on the unit sphere. Thus segmentation must be performed as a pre-processing step, either by hand or by using additional specialized semi-automated segmentation tools, before the SPHARM method can be applied to new volumetric data.

In contrast, because the SWD method is based on an expansion of the whole volume in a series of orthogonal basis functions, therefore it can be reformulated to reconstruct not just the internal volume of the input 3D data, but to produce and emphasize all the interfaces or transitions that exist inside the volume. Mathematically this procedure can be described by taking the square of the gradient of the expansion $|\nabla f(r, \theta, \phi)|^2$, similar to the approach taken by various edge detection techniques used in 2D image processing. This edge detection is essentially the first and the most important step of almost any segmentation technique used in 2D, and the quality of edge detection is crucial for overall success of segmentation process. Using Fourier expansion of 2D images, the gradient calculations can be improved significantly (Gelb and Cates, 2009) both in accuracy and in computational efficiency.

The SWD method is essentially a three-dimensional variant of a Fourier decomposition and most of the results of conventional Fourier series analysis can be transferred (with appropriate modifications) to the spherical wave series. Therefore, the SWD coefficients can be used for interface detection in 3D by efficient and accurate computation of the gradient square. In spherical coordinates the gradient has the following components:

$$\nabla_r = \frac{\partial}{\partial r}, \nabla_\theta = \frac{1}{r}\frac{\partial}{\partial \theta}, \nabla_\phi = \frac{1}{r\sin\theta}\frac{\partial}{\partial \phi}. \quad (21)$$

In order to efficiently compute $|\nabla f(r, \theta, \phi)|^2$ instead of the original volume function $f(r, \theta, \phi)$, each of these components must be applied to the expansion to the expansion in Equation (3).

Using recurrence relations for derivatives of the associated Legendre polynomials $P_l^m(x)$ $$\frac{d}{dx}P_l^m(x) = \frac{1}{1-x^2}[-lxP_l^m(x) + (l+m)P_{l-1}^m(x)], \quad (22)$$

and for derivatives of the spherical Bessel function $j_l(x)$ $$\frac{d}{dx}j_l(x) = j_{l-1}(x) - \frac{l+1}{x}j_l(x). \quad (23)$$

one can update the expansion coefficients and obtain expressions for the gradient components as a new SWD series along each of the orthogonal coordinates:

$$\nabla_\phi f(r, \theta, \phi) = \frac{1}{r\sin\theta}\sum_{n=1}^{\infty}\sum_{l=0}^{\infty}\sum_{m=-l}^{l}(-im)f_{lmn}R_{ln}(r)Y_l^m(\theta, \phi) \quad (24)$$

$$\nabla_\theta f(r, \theta, \phi) = \frac{\cos\theta}{r\sin\theta} \sum_{n=1}^{\infty} \sum_{l=0}^{\infty} \sum_{m=-l}^{l} l f_{lmn} R_{ln}(r) Y_l^m(\theta, \phi) - \quad (25)$$

$$\frac{1}{r\sin\theta} \sum_{n=1}^{\infty} \sum_{l=0}^{\infty} \sum_{m=-l}^{l} (l+m) f_{(l+1)mn} R_{ln}(r) Y_l^m(\theta, \phi)$$

$$\nabla_r f(r, \theta, \phi) = \sum_{n=1}^{\infty} \sum_{l=0}^{\infty} \sum_{m=-l}^{l} k_{ln} f_{lm(n+1)} R_{ln}(r) Y_l^m(\theta, \phi) - \quad (26)$$

$$\frac{1}{r} \sum_{n=1}^{\infty} \sum_{l=0}^{\infty} \sum_{m=-l}^{l} (n+1) f_{lmn} R_{ln}(r) Y_l^m(\theta, \phi).$$

The same SWD procedure described in the previous section can be used to transform these coefficients to spherical and then Cartesian domain. Hence, five SWD transforms will be needed to compute the gradient square.

Figure 5:
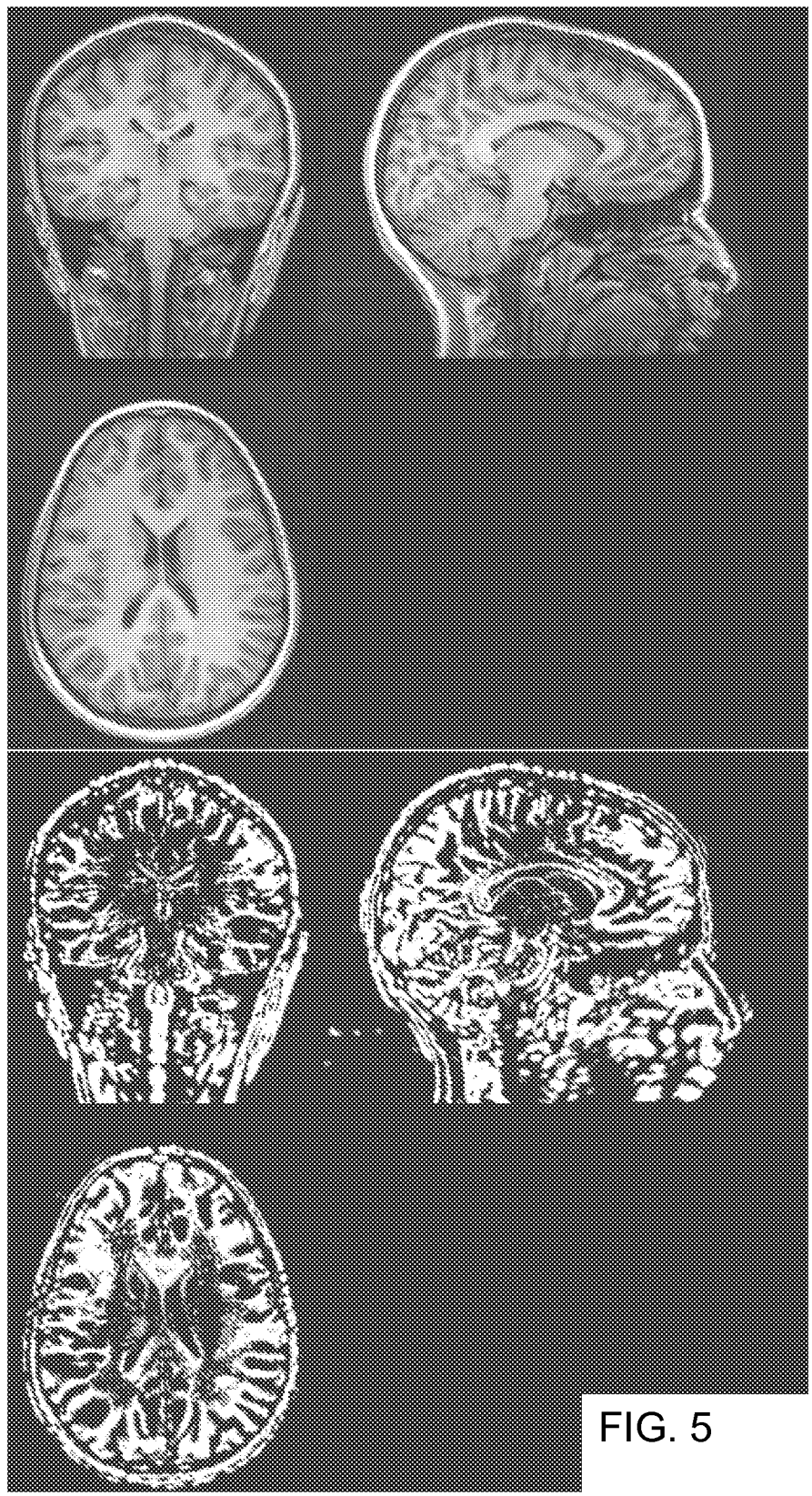
FIG. 5 illustrates images of anatomical data (top) and derivative (bottom) calculated from the SWD coefficients.

An example of the derivatives in human anatomical data is shown in FIGS. 5a and 5b. The lower panel (FIG. 5b), is the derivative calculated from SWD coefficients, which clearly shows detection of interfaces between various tissues present in the original anatomical volumetric data (FIG. 5a), including interfaces between gray and white matter.

This Fourier-based approach for obtaining expressions for the gradient components has several advantages over direct numerical differentiation in the spatial domain. First of all, due to the multiscale nature of the SWD algorithm, it easily allows controlling the scale of the gradients involved in the edge detection process. Moreover, numerical differentiation of noisy data in the spatial domain has inherently low accuracy, whereas the Fourier-based algorithm can significantly improve the accuracy by appropriate choice of filtering.

In practice, fully automated segmentation requires a combination of methods that not only characterizes the shapes of the internal structures, but incorporates some prior information about their spectrum, spatial scales, and spatial distributions. This combination can include the interfaces from the volume gradient to find an initial estimate for intensity thresholds and number of intensity clusters. The low frequency interfaces (actually their positions) can then be included in some sort of topological analysis. Finally, the high frequency interface data can be used to facilitate topological closure of identified low frequency clusters that may be used to update and generate detailed structures.

Figure 6:
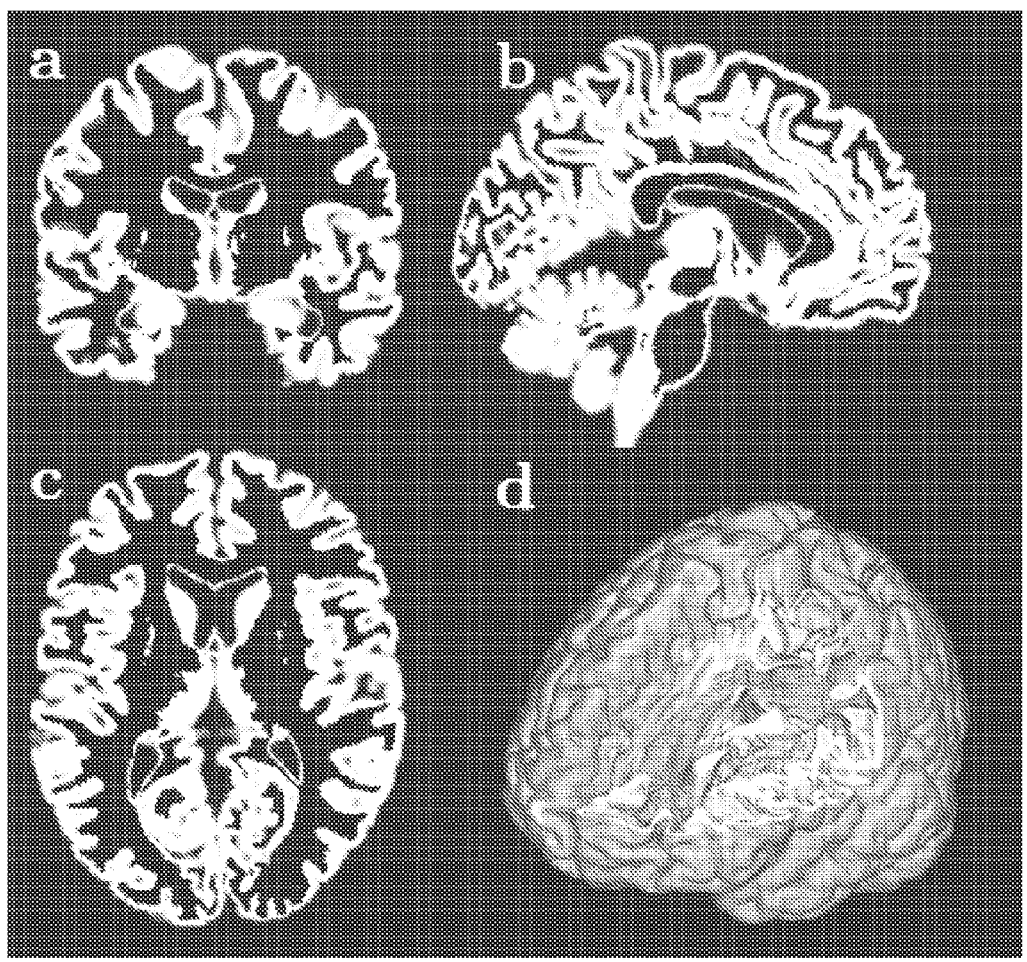
Figure 7:
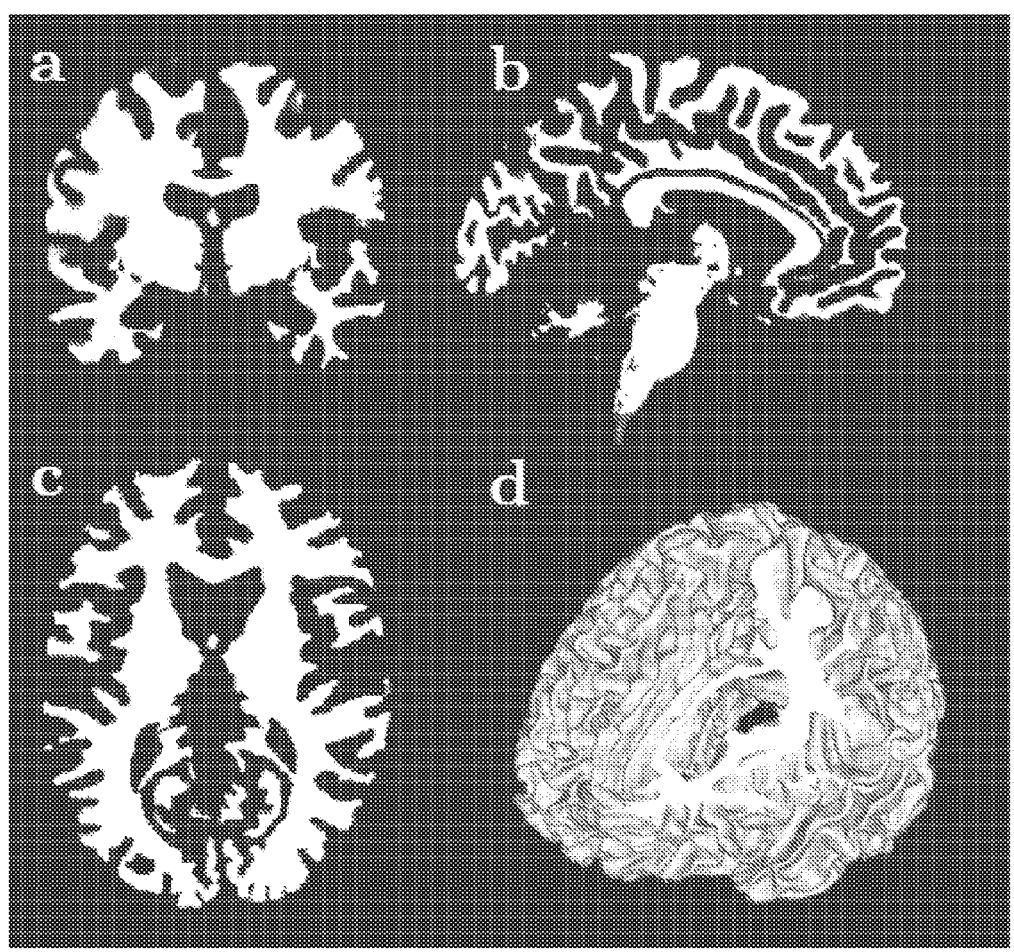

The potential that the present method holds for automatic segmentation can be demonstrated using the derivative map surface for the brain volumetric data that was used in the previous sections for analyses of the SWD accuracy and bandwidth (FIG. 1a). This approach assumes a bimodal structure of the volumetric intensities, but in contrast to most classification techniques, no assumptions were made about the type of a distribution for each of the modes (i.e., it was not treated as Gaussian). The only assumption was that the modes were well separated. The derivative map was applied to estimate an intensity threshold $I_t$ by calculating an average intensity inside all regions with large values of intensity gradient $$I_t = \sum_{|\nabla f| > \nabla_f} f(x, y, z) \Big/ \sum_{|\nabla f| > \nabla_f} 1, \quad (27)$$

where $\nabla_f = \overline{|\nabla f|}$. This simplified illustrative procedure still provided accurate segmentation between gray and white matter in a completely automatic manner. Panels a-c of FIG. 6 show gray matter slices, while panel d shows a 3D view. Panels a-c of FIG. 7 show white matter slices; panel d shows a 3D view.

All types of SWD-based analyses described in the previous sections (including weighted Fourier smoothing, optimal SWD order and volume morfometry/complexity) are similarly applicable to these segmented out and independently represented brain structures. Thus, the average gray matter density, the cortical thickness, as well as various local abnormalities, can be accurately calculated directly from the volumetric data on different scales (i.e. using different degrees of smoothness). This is in contrast to the SPHARM, where both the gray matter density and the cortical thickness can only be approximated through a distance map between independently fitted inner and outer cortical surfaces (Chung et al., 2007). This process is prone to various sources of errors, the most important of which are from surface registration, mesh construction and discrete thickness computation, and is very sensitive to presence of noise.

Example 4: Comparison of SWD to Free-Surfer/SPHARM Analysis

To test the efficacy of present approach in real life applications as well as to compare with the current state-of-the-art methods a complete analysis work-flow of brain segmentation/characterization task was conducted using the original 3D brain dataset (FIG. 1a) as an input to FreeSurfer/SPHARM combination. As the SPHARM on its own is unable to analyze volumetric data, the typical analysis work-flow requires as a first step preprocessing of the volumetric data with FreeSurfer (Dale et al., 1999). FreeSurfer is a set of tools for analysis and visualization of structural and functional brain imaging data developed at the Martinos Center for Biomedical Imaging. FreeSurfer contains a fully automatic structural imaging stream for processing cross-sectional and longitudinal data. At this stage white matter surface was extracted using all the required steps of the standard FreeSurfer processing, i.e., segmentation, inflation, registration, fitting to sphere, etc. The total FreeSurfer processing took more than 12 hours to obtain a single hemisphere white matter surface.

The resulting white matter surface of the left hemisphere was used afterwards as an input to several different stages of the weighed spherical harmonic (weighted-SPHARM) representation created by Moo K. Chung at the the Department of Biostatistics and Medical Informatics, Waisman Laboratory for Brain Imaging and Behavior at the University of Wisconsin-Madison. The weighted-SPHARM representation is a unified surface data smoothing, surface parametrization and surface registration technique formulated in a unified Hilbert space framework. The weighted-SPHARM expresses surface data as a weighted linear combination of spherical harmonics. The weighted-SPHARM generalizes the traditional SPHARM representation as a special case.

The first SPHARM step is to construct the spherical harmonics representation and save it into a hard drive (~2.86 GB). This step took around 7 minutes for generating all the harmonics up to $L_{max}=85$. ($L_{max}=85$ was chosen due to the inability of the SPHARM to produce higher degree expansion—an error message stating "matrix is singular to working precision" was displayed for any degree above 85). The WFS smoothing step (SPHARMsmooth2) of the SPHARM took about 30 minutes using the same degree $L_{max}=85$.

Generation of the smoothed white matter surface from a set of Fourier coefficients (SPHARMrepresent2) took around 20 minutes. The overall processing of the left hemisphere white matter surface took close to 14 hours (the processing times are summarized in Table 2). The total FreeSurfer processing of both hemispheres as well as the gray matter surfaces took almost a day (>23 hours).

TABLE 2

| Steps | | SPHARM[a] | SWD |
|---|---|---|---|
| | FreeSurfer | 12 hours 50 min[b] | |
| | SPHARMconstruct | 420 sec | |
| | SPHARMsmooth2 | 1064 sec | |
| | SPHARMrepresent2 | 740 sec[c] | |
| | Total time | ~14 hours | ≲ 10 sec[d] |

[a]SPHARM only works for $L_{max}$ up to 85, hence in all timings $L_{max}$ = 85 is used
[b]FreeSurfer time is for the left hemisphere only, add 4.5 hours for both
[c]SPHARMsmooth2 step also includes the SPHARMrepresent2 step
[d]SWD total time includes both the expansion and the derivative calculations for $L_{max}$ = 100 (5.34 sec) and the segmentation step for $L_{max}$ = 85 (3.55 sec)

Figure 8A:
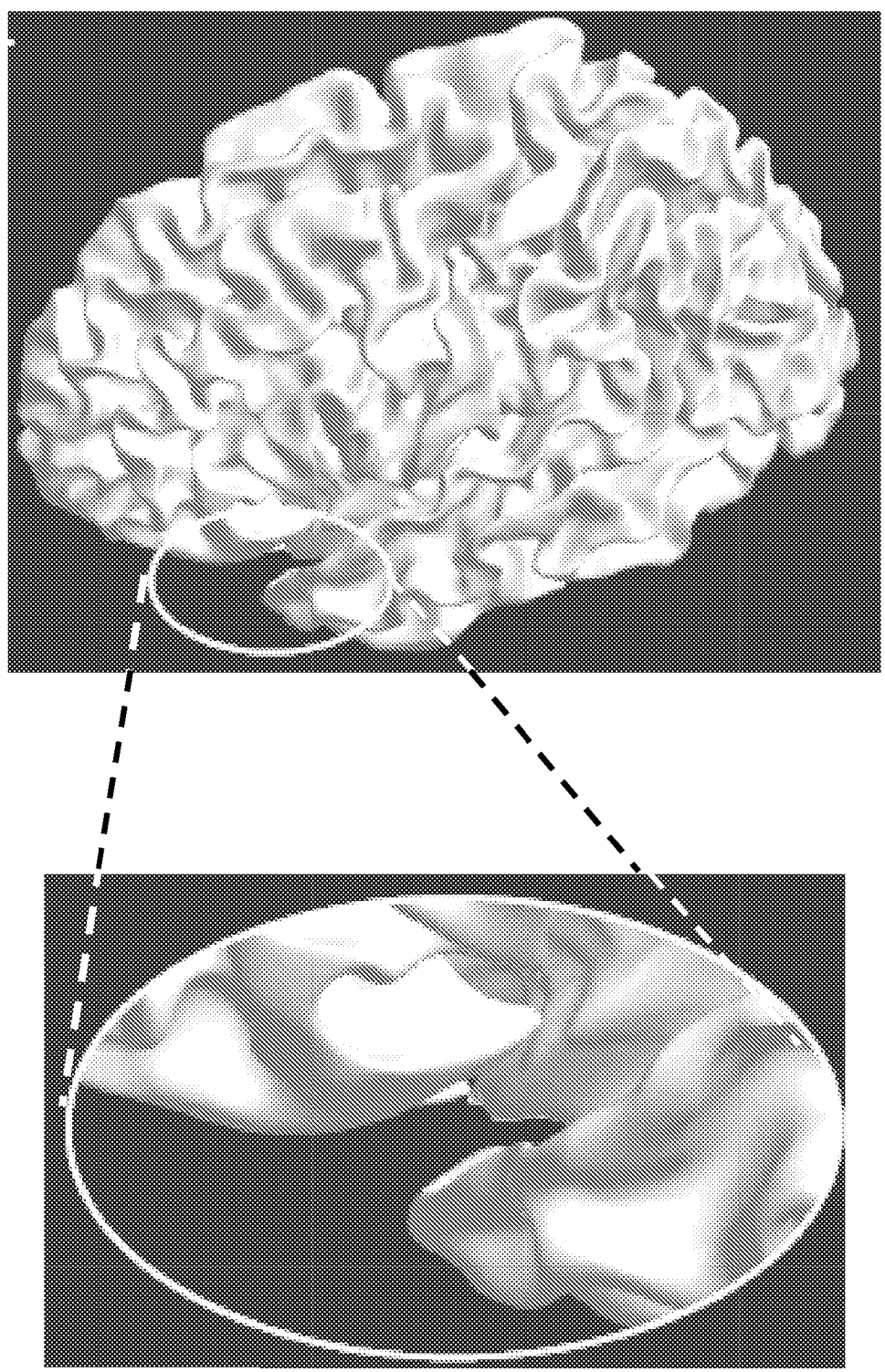
FIGS. 8a and 8b illustrate images of 3D views of white matter of a left hemisphere of the brain obtained from the full 3D brain in FIG. 1a using a SPHARM and SWD method, respectively.
Figure 8B:
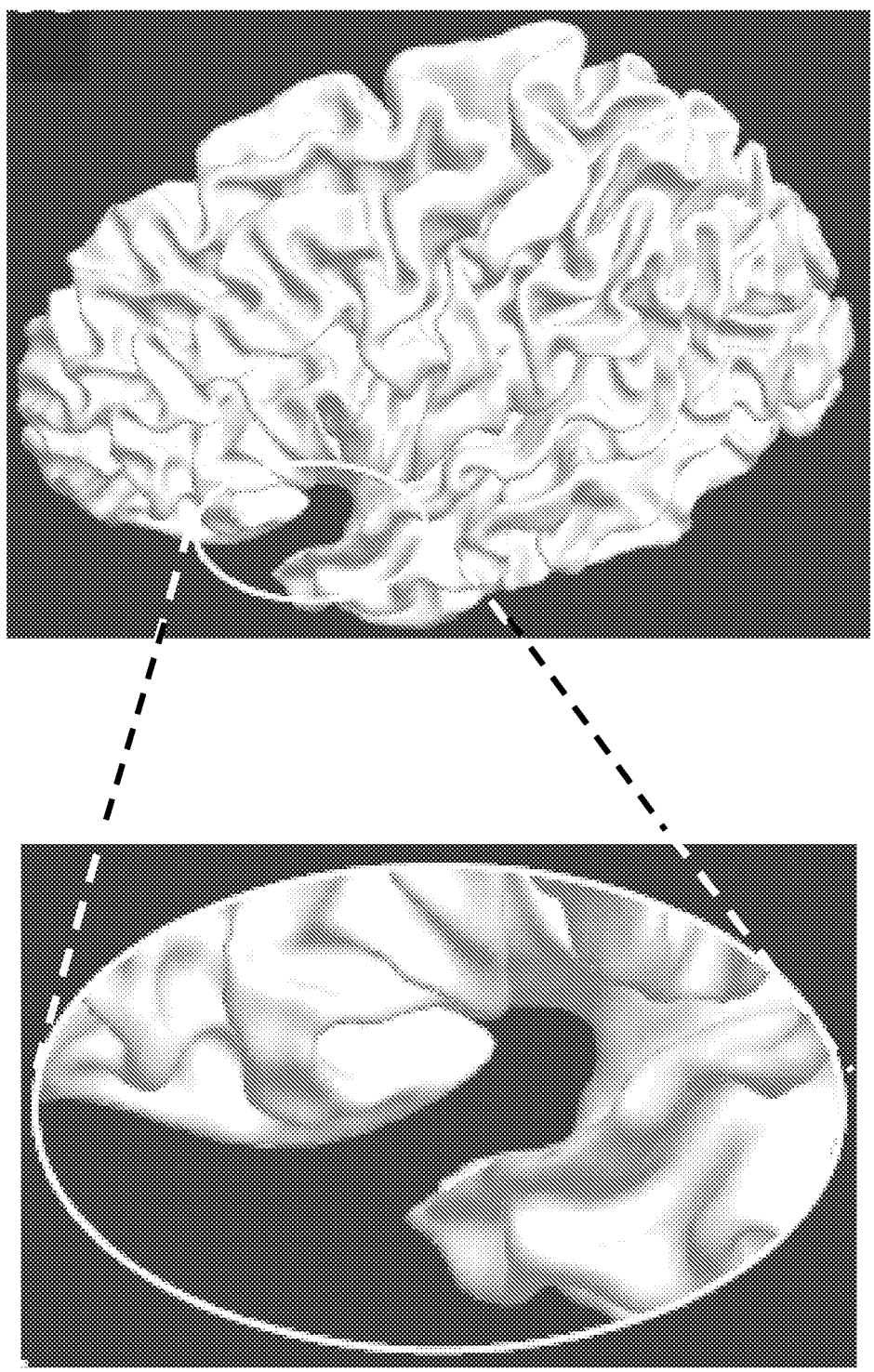

FIGS. 8a and 8b show the 3D views of both the SPHARM and the SWD white matter extraction results, respectively. The details as well as the quality of the segmentation seems to be comparable for the SPHARM and for the SWD results, however, topological defects produced by a single sphere inflation procedure of FreeSurfer followed by smoothing of the SPHARM are clearly visible in the SPHARM surface, seen in the circled area of the upper panel and zoomed in detail of FIG. 8a. Such defects are absent in the corresponding SWD image and detail of FIG. 8b.

Figure 9A:
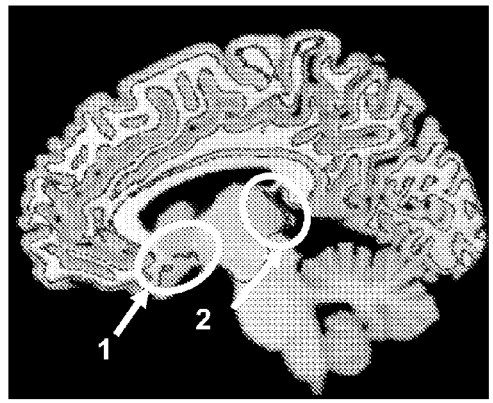
FIGS. 9a-9f illustrate two slices of white matter surface obtained from FreeSurfer/SPHARM analysis, where
Figure 9B:
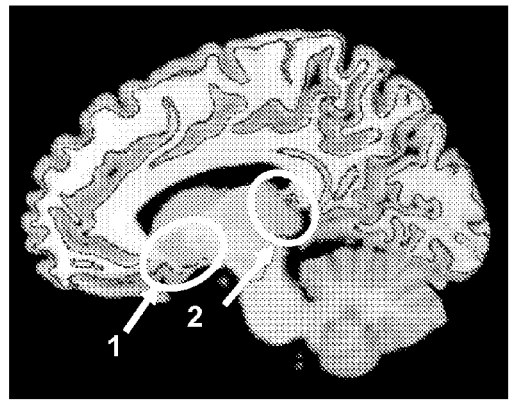
Figure 9C:
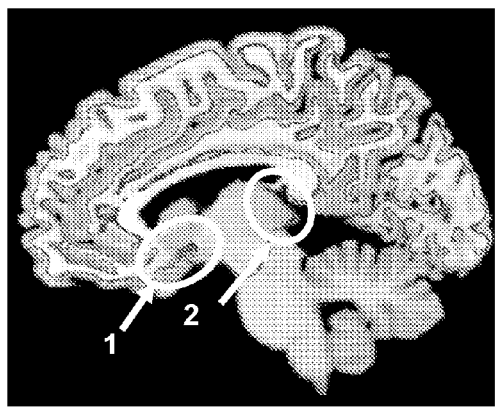
Figure 9D:
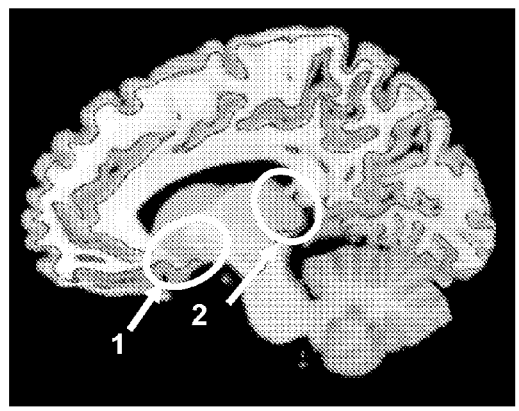
Figure 9E:
Figure 9F:
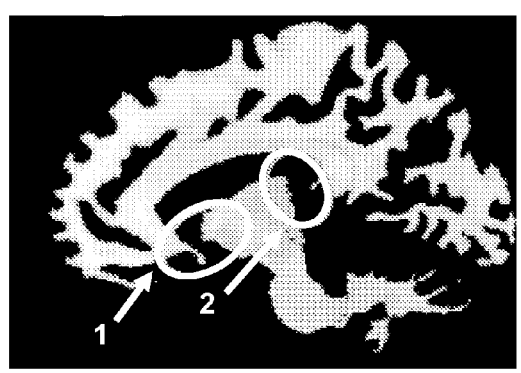

The reason for these topological defects can be understood by looking at sample slices of the volumetric data with the SPHARM/FreeSurfer white matter surface overlaid. FIGS. 9a and 9b show original FreeSurfer segmentation results. FIGS. 9c and 9d show the final surface obtained with SPHARM smoothing. Circled area 1 shows the same defect that was highlighted in the FIG. 8a. Another defect area, circled area 2, is located deep inside the volume. The bridging of both of these areas results in topologically incorrect surface closure and produces convex region that actually encompass hollow area inside this topologically closed white matter region. This erroneous bridging is absent on slides of volumetric SWD white matter shown in FIGS. 9e and 9f.

The above-described spherical wave decomposition (SWD) method allows compact representation, characterization, automatic segmentation and morphometry analysis of complex shapes embedded within volumetric data. The method is general and thus applicable to a wide range of applications. While the foregoing examples are directed to quantitative analysis of volumetric magnetic resonance imaging data, the SWD method is also applicable to other types of medical imaging data as well as any application involving characterization of volumetric data. Potential applications include geological structure modeling and visualization, and visualization of weather data.

The SWD representation uses a direct expansion of volumetric data in a linear combination of basis functions that include both angular (spherical harmonics) and radial (spherical Bessel functions) parts. The 3D descriptors are easily archived and facilitate statistical comparison at multiple spatial scales: low frequency information describes gross shape, while high frequency information captures more detail as well as internal structures.

In contrast to surface based methods, the SWD approach does not require an initial segmentation of a surface and a subsequent inflation of this surface to satisfy the uniqueness or stability of subsequent surface fitting algorithms. The surface methods are inefficient and time consuming because of the need for segmentation prior to fitting and the computationally intensive inflation process, the latter of which being also a significant source of errors due to creation of topological defects.

Implementation of the SWD method is based on several fast transforms for spherical harmonics and spherical Bessel functions and, therefore, is significantly faster than conventional surface based methods, but at the same time provides significantly higher accuracy. The fast transforms for spherical Bessel functions are based on a novel expression for asymptotic expansion as $1/k^n$ series of the standard sine and cosine Fourier transforms and rearrangement of coefficients obtained by the standard FFTs afterwards.

Overall, the SWD method is uniquely positioned to provide an effective, accurate and robust approach for morphology characterization, segmentation, and comparative morphometry for both basic neuroscience studies on comparative brain anatomy and clinical studies of disease characterization and progression in humans, and for a broad range of studies in comparative biology.

The above-described method may be implemented using a general or special purpose computer system. For example, the system may be incorporated into or be in communication with a clinical decision support system (CDSS) for assisting health care professionals with decision making tasks at the point of care. Embodiments herein may be embodied on a computer program product, stored on a computer readable medium and executed on a computer with a processor and a memory.

Figure 10:
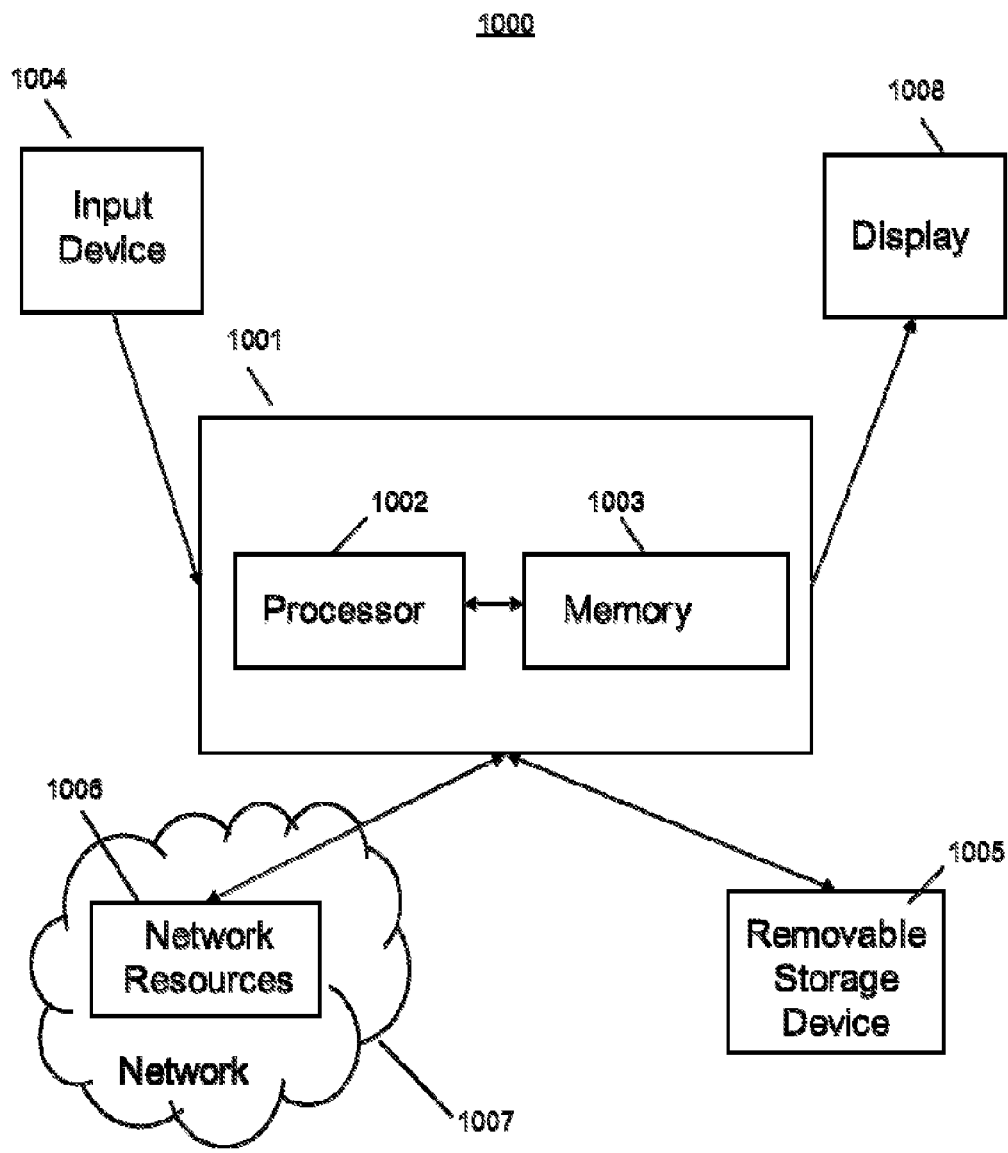
FIG. 10 is a block diagram that illustrates an embodiment of a computer/server system upon which an embodiment of the inventive methodology may be implemented.

FIG. 10 is a block diagram that illustrates an exemplary embodiment of a computer/server system 1000 upon which an embodiment of the inventive methodology may be implemented. The system 1000 includes a computer/server platform 1001 including a processor 1002 and memory 1003 which operate to execute instructions, as known to one of skill in the art. The term "computer-readable storage medium" as used herein refers to any tangible medium, such as a disk or semiconductor memory, that participates in providing instructions to processor 1002 for execution. Additionally, the computer platform 1001 receives input from a plurality of input devices 1004, such as a keyboard, mouse, touch device or verbal command. The computer platform 1001 may additionally be connected to a removable storage device 1005, such as a portable hard drive, optical media (CD or DVD), disk media or any other tangible medium from which a computer can read executable code. The computer platform may further be connected to network resources 1006 which connect to the Internet or other components of a local public or private network. The network resources 1006 may provide instructions and data to the computer platform from a remote location on a network 1007. The connections to the network resources 1006 may be via wireless protocols, such as the 802.11 standards, Bluetooth® or cellular protocols, or via physical transmission media, such as cables or fiber optics. The network resources may include storage devices for storing data and executable instructions at a location separate from the computer platform 1001. The computer interacts with a display 1008 to output data and other information to a user, as well as to request additional instructions and input from the user. The display 1008 may therefore further act as an input device 1004 for interacting with a user.

Figure 11:
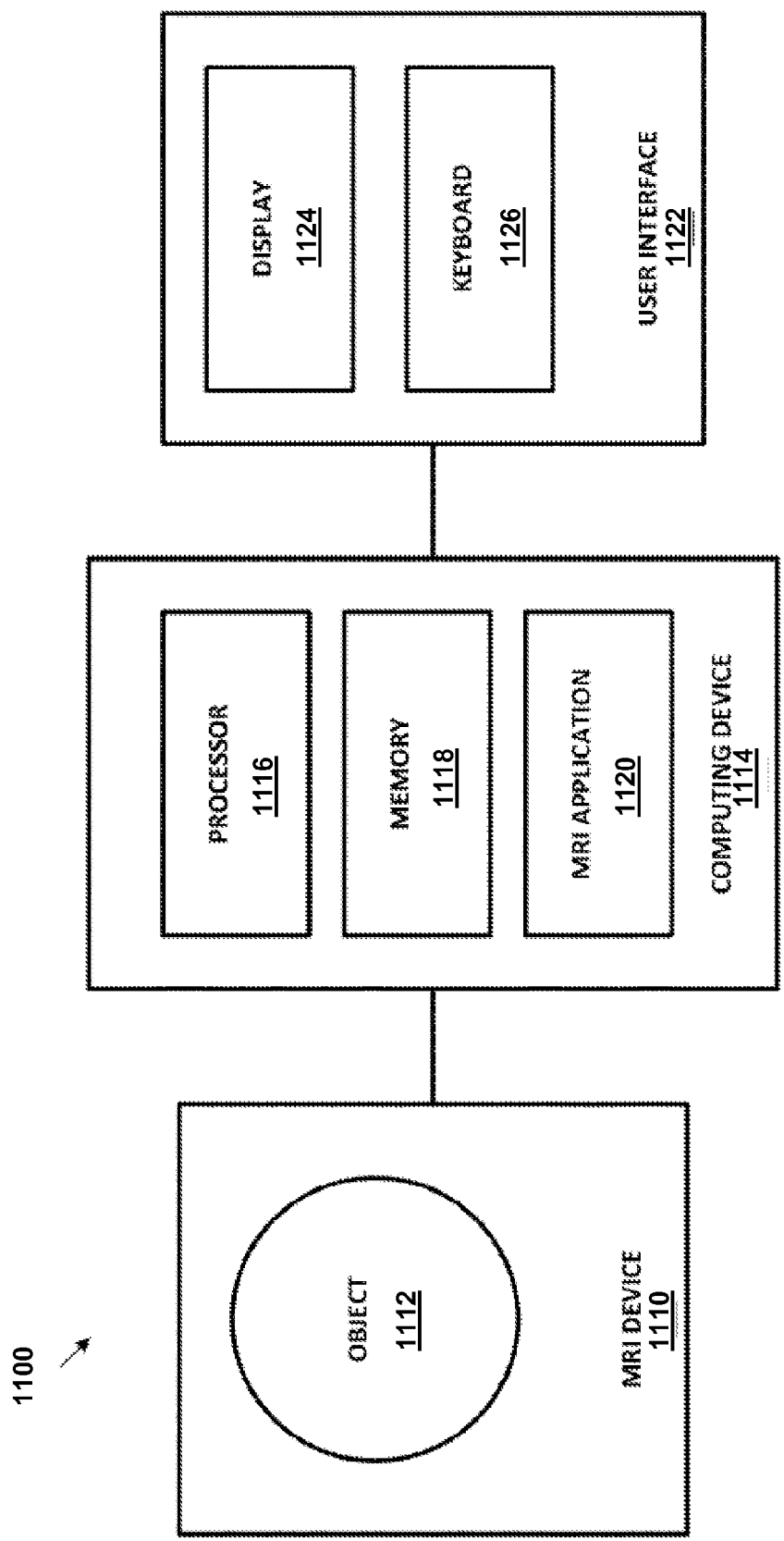
FIG. 11 is a block diagram of an exemplary MRI system upon which an embodiment of the inventive methodology may be implemented.

FIG. 11 illustrates an exemplary block diagram of an MRI system 1100 in accordance with embodiments of the present disclosure. Referring to FIG. 11, the system 1100 may include an MRI device 1110. The MRI device 1110 may be configured for scanning and capturing an image of an object 1112 such as an anatomical image of an object. Example objects to be imaged include, but are not limited to, liver tissue, brain tissue, kidney tissue, heart tissue, and other bodily tissues. The MRI system may include a computing device 1114 having communicative connection to the MRI device 1110. The computing device 1114 may include a processor 1116, a memory 1118, and an MRI application 1120 that is configured to execute on the processor 1116. The MRI system 1110 may include a user interface 1122, such as an image generator, that is configured to display images on a display 1124 and to receive user input through a user input device, such as, for example, a keyboard 1126.

Figure 12:
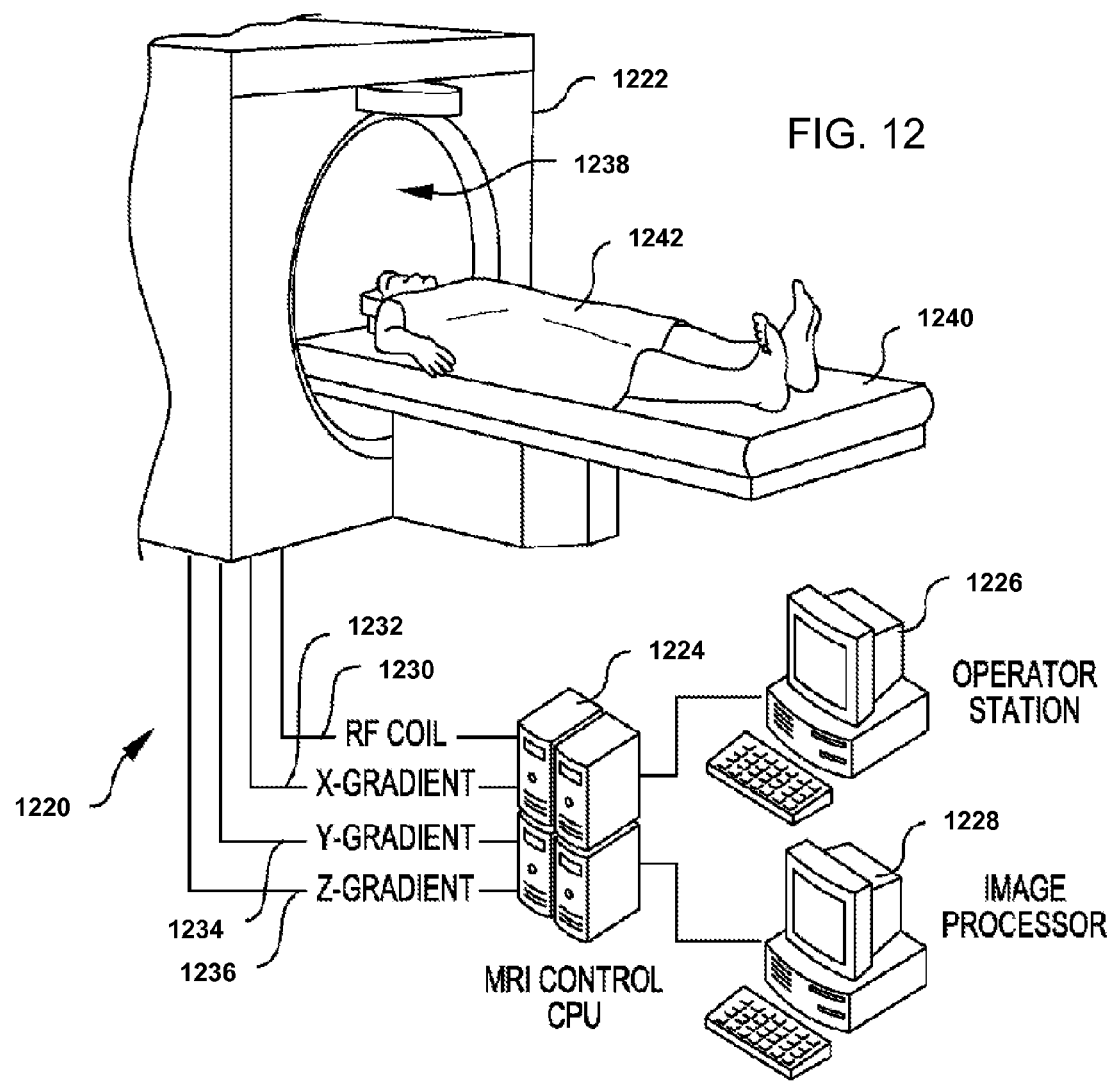
FIG. 12 shows an exemplary imaging system that may be used in conjunction with the inventive methodology.

FIG. 12 shows an exemplary imaging system 1220 that may be used in conjunction with the SWD method. The imaging system 1220 includes a scanner 1222 in communication with a control CPU 1224 for controlling the scanner 1222, an operator station 1226 for allowing human control of the control CPU 1224 and scanner 1222, and an image processor 1228 for analyzing images of subjects scanned by the scanner 1222.

The scanner 1222 can be any device capable of measuring data from an object, such as a person, for later processing into images. In an embodiment the scanner 1222 is a Magnetic Resonance Imaging (MRI) scanner and includes a radio frequency (RF) coil 30, an x-gradient 1232, a y-gradient 1234, and a z-gradient 1236, all controlled by the control CPU 1224. The scanner 1222 operates by creating a uniform magnetic field around an object to be scanned and emitting through the RF coil 1230 radio waves into the subject. The x gradient 1232, y gradient 2134, and z gradient 1236 are operated by the control CPU 1224 so as to control the location in the subject being scanned.

Generally, scanners such as the scanner 1222 include a chamber 1238 from which a table 1240 extends. Typically, a patient 1242 or other subject lies on the table 1240 which is mechanically operated so as to place the patient 1242 into the chamber 1238 for scanning.

The above description of disclosed embodiments is provided to enable any person skilled in the art to make or use the invention. Various modifications to the embodiments will be readily apparent to those skilled in the art, the generic principals defined herein can be applied to other embodiments without departing from spirit or scope of the invention. Thus, the invention is not intended to be limited to the embodiments shown herein but is to be accorded the widest scope consistent with the principals and novel features disclosed herein.

REFERENCES

Abbott, L. F., Schaefer, R. K., 1986. A general, gauge-invariant analysis of the cosmic microwave anisotropy. ApJ 308, 546-562. doi:10.1086/164525.

Atkins, M. S., Mackiewich, B. T., 2000. Fully automated hybrid segmentation of the brain. Handbook of Medical Imaging, Processing and Analysis, 171-183.

Barnett, A., 1996. The calculation of spherical Bessel functions and Coulomb functions. Computational Atomic Physics: Electron and Positron Collisions with Atoms and Ions, 181-202.

Barnett, A. R., 1981. An algorithm for regular and irregular Coulomb and Bessel functions of real order to machine accuracy. Computer Physics Communications 21, 297-314. doi:10.1016/0010-4655(81)90011-4.

Barra, V., Boire, J. Y., 2000. Tissue segmentation on MR images of the brain by possibilistic clustering on a 3D wavelet representation. J Magn Reson Imaging 11, 267-278.

Barra, V., Boire, J. Y., 2001. Automatic segmentation of subcortical brain structures in MR images using information fusion. IEEE Trans Med Imaging 20, 549-558.

Barra, V., Boire, J. Y., 2002. Segmentation of fat and muscle from MR images of the thigh by a possibilistic clustering algorithm. Comput Methods Programs Biomed 68, 185-193.

Binney, J., Quinn, T., 1991. Gaussian random fields in spherical coordinates. MNRAS 249, 678-683.

Bisseling, R., Kosloff, R., 1985. The fast Hankel transform as a tool in the solution of the time dependent Schrodinger equation. Journal of Computational Physics 59, 136-151.

Brechbuhler, C., Gerig, G., Kubler, O., 1995. Parametrization of Closed Surfaces for 3-D Shape Description. Computer Vision and Image Understanding 61 (2), 154-170.

Chung, M. K., Dalton, K. M., Shen, L., Evans, A. C., Davidson, R. J., 2007. Weighted Fourier Series Representation and Its Application to Quantifying the Amount of Gray Matter. IEEE Trans. Med. Imaging 26 (4), 566-581.

Chung, M. K., Dalton, K. M., Davidson, R. J., 2008. Tensor-Based Cortical Surface Morphometry via Weighted Spherical Harmonic Representation. IEEE Trans. Med. Imaging 27 (8), 1143-1151.

Cocuzzo, D., Lin, A., Ramadan, S., Mountford, C., Keshava, N., 2011. Algorithms for characterizing brain metabolites in two-dimensional in vivo MR correlation spectroscopy. Conf Proc IEEE Eng Med Biol Soc 2011, 4929-4934.

Dale, A. M., Fischl, B., Sereno, M. I., 1999. Cortical surface-based analysis. I. Segmentation and surface reconstruction. Neuroimage 9, 179-194.

Driscoll, J. R., Healy, D. M., 1994. Computing Fourier transforms and convolutions on the 2-sphere. Advances in applied mathematics 15, 202-250.

Gelb, A., 1997. The resolution of the Gibbs phenomenon for spherical harmonics. Mathematics of Computation 66, 699-717.

Gelb, A., Cates, D., 2009. Segmentation of images from fourier spectral data. Commun Comput. Phys. 5, 326-349.

Gersten, A., 1971. Wavefunction Expansion in Terms of Spherical Bessel Functions. Journal of Mathematical Physics 12, 924-929. doi:10.1063/1.1665682.

He, Q., Karsch, K., Duan, Y., 2011. Semi-automatic 3D segmentation of brain structures from MRI. Int J Data Min Bioinform 5, 158-173.

Healy, Jr., D., Rockmore, D., Kostelec, P. J., Moore, S. S. B., 1996. FFTs for the 2-Sphere-Improvements and Variations. The Journal of Fourier Analysis and Applications 9, 341-385.

Healy, Jr., D. M., Kostelec, P. J., Rockmore, D. N., 2004. Towards Safe and Effective High-Order Legendre Transforms with Applications to FFTs for the 2-sphere. Adv. Comput. Math. 21, 59-105.

Kazhdan, M. M., Funkhouser, T. A., Rusinkiewicz, S., 2003. Rotation Invariant Spherical Harmonic Representation of 3D Shape Descriptors. In: Kobbelt, L., Schroder, P., Hoppe, H. (Eds.), Symposium on Geometry Processing. Vol. 43 of ACM International Conference Proceeding Series. Eurographics Association, pp. 156-164.

Kiebel, S. J., Goebel, R., Friston, K. J., 2000. Anatomically informed basis functions. Neuroimage 11, 656-667.

Klauschen, F., Goldman, A., Barra, V., Meyer-Lindenberg, A., Lundervold, A., 2009. Evaluation of automated brain MR image segmentation and volumetry methods. Hum Brain Mapp 30, 1310-1327.

Klein, A., Andersson, J., Ardekani, B. A., Ashburner, J., Avants, B., Chiang, M. C., Christensen, G. E., Collins, D. L., Gee, J., Hellier, P., et al., 2009. Evaluation of 14 nonlinear deformation algorithms applied to human brain MRI registration. Neuroimage 46, 786.

Koval, P., Talman, J. D., 2010. Update of spherical Bessel transform: FFTW and OpenMP. Computer Physics Communications 181, 2212-2213.

Lebedev, N., 1972. Special functions and their applications. Revised edition, translated from the Russian and edited by Richard A. Silverman. Unabridged and corrected republication. Dover Publications, Inc., New York.

Leistedt, B., Rassat, A., Refregier, A., Starck, J. L., 2012. 3DEX: a code for fast spherical Fourier-Bessel decomposition of 3D surveys. A&A 540, A60. doi:10.1051/0004-6361/201118463, arXiv:1111.3591.

Li, S., 1994. Markov random field models in computer vision, in: Eklundh, J. O. (Ed.), Computer Vision ECCV '94. Springer Berlin Heidelberg. volume 801 of Lecture Notes in Computer Science, pp. 361-370.

Liang, Z., MacFall, J., Harrington, D., 1994. Parameter estimation and tissue segmentation from multispectral MR images. Medical Imaging, IEEE Transactions on 13, 441-449. doi:10.1109/42.310875.

Lin, G. C., Wang, W. J., Kang, C. C., Wang, C. M., 2012. Multispectral MR images segmentation based on fuzzy knowledge and modified seeded region growing. Magn Reson Imaging 30, 230-246.

Mangin, J. F., Frouin, V., Bloch, I., Regis, J., Lopez-Krahe, J., 1995. From 3D magnetic resonance images to structural representations of the cortex topography using topology preserving deformations. Journal of Mathematical Imaging and Vision 5, 297-318.

Mohlenkamp, M. J., 1999. A fast transform for spherical harmonics. Journal of Fourier analysis and applications 5, 159-184.

Pachai, C., Zhu, Y. M., Guttmann, C. R. G., Kikinis, R., Jolesz, F. A., Gimenez, G., Froment, J. C., Confavreux, C., Warfield, S. K., 2001. Unsupervised and Adaptive Segmentation of Multispectral 3D Magnetic Resonance Images of Human Brain: A Generic Approach, in: Niessen, W. J., Viergever, M. A. (Eds.), MICCAI, Springer. pp. 1067-1074.

Pedoia, V., Binaghi, E., 2012. Automatic MRI 2D brain segmentation using graph searching technique. International Journal for Numerical Methods in Biomedical Engineering URL: http://dx.doi.org/10.1002/cnm 2498, doi: 10.1002/cnm 2498.

Pettitt, B. A., Danchura, W., Labun, D., 1993. Spherical Bessel Transforms. Journal of Computational Physics 105, 178-181. doi:10.1006/jcph.1993.1064.

Pham, D. L., Prince, J. L., 1999. An adaptive fuzzy C-means algorithm for image segmentation in the presence of intensity inhomogeneities. Pattern Recognition Letters 20, 57-68.

Pham, D. L., Xu, C., Prince, J. L., 2000. A Survey of Current Methods in Medical Image Segmentation, in: Annual Review of Biomedical Engineering. volume 2, pp. 315-338.

Popuri, K., Cobzas, D., Murtha, A., Jagersand, M., 2012. 3D variational brain tumor segmentation using Dirichlet priors on a clustered feature set. Int J Comput Assist Radiol Surg 7, 493-506.

Razlighi, Q. R., Orekhov, A., Laine, A., Stern, Y., 2012. Causal Markov random field for brain MR image segmentation. Conf Proc IEEE Eng Med Biol Soc 2012, 3203-3206.

Rokhlin, V., Tygert, M., 2006. Fast algorithms for spherical harmonic expansions. SIAM Journal on Scientific Computing 27, 1903-1928.

Sharafeddin, O. A., Ferrel Bowen, H., Kouri, D. J., Hoffman, D. K., 1992. Numerical Evaluation of Spherical Bessel Transforms via Fast Fourier Transforms. Journal of Computational Physics 100, 294. doi:10.1016/0021-9991(92)90236-R.

Suri, J. S., 2001. Two-dimensional fast magnetic resonance brain segmentation. IEEE Eng Med Biol Mag 20, 84-95.

Talman, J. D., 1978. Numerical Fourier and Bessel Transforms in Logarithmic Variables. Journal of Computational Physics 29, 35. doi:10.1016/0021-9991(78)90107-9.

Talman, J. D., 2009. NumSBT: A subroutine for calculating spherical Bessel transforms numerically. Computer Physics Communications 180, 332-338.

Toyoda, M., Ozaki, T., 2010. Fast spherical Bessel transform via fast Fourier transform and recurrence formula. Computer Physics Communications 181, 277-282.

Wels, M., Zheng, Y., Huber, M., Hornegger, J., Comaniciu, D., 2011. A discriminative model-constrained EM approach to 3D MRI brain tissue classification and intensity non-uniformity correction. Phys Med Biol 56, 3269-3300.

Zavaljevski, A., Dhawan, A. P., Gaskil, M., Ball, W., Johnson, J. D., 2000. Multi-level adaptive segmentation of multi-parameter MR brain images. Comput Med Imaging Graph 24, 87-98.

Zelditch, M., Swiderski, D., Sheets, H., Fink, W., 2004. Geometric Morphometrics for Biologists: A Primer. Elsevier Science.

The invention claimed is:

1. A method for generating a three-dimensional model of brain morphology, comprising:

acquiring, via an imaging system, volumetric MRI data for a subject's brain, the volumetric MRI data comprising three-dimensional datapoints comprising Cartesian coordinates;

inputting the volumetric MRI data into a computer processor having instructions stored therein for causing the computer processor to execute the steps of:

transforming the volumetric MRI data into spherical coordinates comprising radial and angular variables and computing spherical wave decomposition by;

expanding the transformed spherical coordinates into 3D basis functions by:

expanding angular variables into angular-only spherical harmonic basis functions having preselected angular degree to determine angular coefficients; and expanding the radial variables into radial basis functions having preselected radial degrees by asymptotic expansion as a series of sine and cosine Fourier transforms to determine radial coefficients, wherein the series of sine and cosine Fourier transforms have the form $$f(k, \theta, \phi) = \sum_{n=0}^{l} \frac{P_l^{(n)}(1)}{k^{n+1}} \times \begin{cases} (-1)^{\lfloor \frac{l-n}{2} \rfloor} \int_0^\infty r^{1-n} dr \sin(kr) f(r, \theta, \phi), & l+n \text{ is even} \\ (-1)^{\lfloor \frac{l-n+1}{2} \rfloor} \int_0^\infty r^{1-n} dr \cos(kr) f(r, \theta, \phi), & l+n \text{ is odd} \end{cases},$$

where [x] denotes the largest integer that does not exceed x, and $P_l^{(N)}$ is a series of Legendre polynomials;

combining angular coefficients and radial coefficients to construct a signature for a 3D volume representation of the brain morphology in spherical coordinates;

transforming the signature into a 3D volume representation of the brain morphology into Cartesian coordinates; and displaying the transformed 3D volume representation of the brain morphology on a graphical user interface.

2. The method of claim 1, wherein the step of transforming the volumetric data comprises convolving the volumetric data with a resampling filter having the form $$f(r) = \iiint \tilde{\vartheta}_x(x-x') f(x') d^3x'.$$

3. The method of claim 2, wherein the resampling filter is balanced between speed and quality by varying between nearest neighbor to complex multipoint interpolation.

4. The method of claim 1, wherein the step of transforming the 3D volume representation comprises convolving the 3D volume data with a resampling filter having the form $$f(x) = \iiint \tilde{\vartheta}_r(r-r') f(r') dV'.$$

5. The method of claim 4, wherein the resampling filter is balanced between speed and quality by varying between nearest neighbor to complex multipoint interpolation.

6. A computer-program product embodied in a non-transitory computer-readable medium which, when executed by a computer processor cause the processor to generate a three-dimensional model of brain morphology by:

receiving volumetric data generated by an MRI scanning system for a subject's brain scan, the volumetric data comprising 3-dimensional data points comprising Cartesian coordinates;

transforming the volumetric data into spherical coordinates comprising radial and angular variables;

computing spherical wave decomposition (SWD) by expanding the transformed spherical coordinates into 3D basis functions by:

expanding angular variables into angular-only spherical harmonic basis functions having preselected angular degrees to determine angular coefficients; and expanding the radial variables into radial basis functions having preselected radial degrees by asymptotic expansion as a series of sine and cosine Fourier transforms to determine radial coefficients;

combining angular coefficients and radial coefficients to construct a signature for a 3D volume representation of the brain morphology in spherical coordinates;

transforming the signature into a 3D volume representation of the brain morphology into Cartesian coordinates; and displaying the transformed 3D volume representation of the brain morphology on a graphical user interface in communication with the computer processor.

7. A computer-program product embodied in a non-transitory computer-readable medium which, when executed by a computer processor, cause the processor to model brain morphology of a subject's brain from input volumetric MRI data by:

combining angular-only basis functions of SPHARM with radial basis functions comprising a series of sine and cosine Fourier transforms to form a complete 3D basis;

expanding the input volumetric MRI data using the complete 3D basis to generate a signature for brain morphology; and generating an output comprising displaying a 3D volume representation of the brain morphology.

8. The computer-program product of claim 7, wherein the step of combining includes:

transforming the volumetric data into spherical coordinates comprising radial and angular variables; and expanding angular variables into spherical harmonic basis functions to determine angular coefficients and expanding radial variables into radial basis functions to determine radial coefficients.

9. The computer-program product of claim 7, wherein the step of generating comprises transforming the 3D volume representation of the structure into Cartesian coordinates.

10. The computer-program product of claim 6, wherein the computer processor transforms the volumetric data by convolving the volumetric data with a resampling filter having the form $$f(r) = \iiint \tilde{\vartheta}_x(x-x') f(x') d^3x'.$$

11. The computer-program product of claim 10, wherein the resampling filter is balanced between speed and quality by varying between nearest neighbor to complex multipoint interpolation.

12. The computer-program product of claim 6, wherein the computer processor transforms the 3D volume representation by convolving the 3D volume data with a resampling filter having the form $$f(x) = \iiint \tilde{\vartheta}_r(r-r') f(r') dV'.$$

13. The computer-program product of claim 12, wherein the wherein the resampling filter is balanced between speed and quality by varying between nearest neighbor to complex multipoint interpolation.

14. The computer-program product of claim 6, wherein the series of sine and cosine Fourier transforms have the form:

$$f(k, \theta, \phi) = \sum_{n=0}^{l} \frac{P_l^{(n)}(1)}{k^{n+1}} \times \begin{cases} (-1)^{\lfloor \frac{l-n}{2} \rfloor} \int_0^\infty r^{1-n} dr \sin(kr) f(r, \theta, \phi), & l+n \text{ is even} \\ (-1)^{\lfloor \frac{l-n+1}{2} \rfloor} \int_0^\infty r^{1-n} dr \cos(kr) f(r, \theta, \phi), & l+n \text{ is odd} \end{cases},$$

where [x] denotes the largest integer that does not exceed x, and $P_l^{(N)}$ is a series of Legendre polynomials.

15. The computer-program product of claim 7, wherein the series of sine and cosine Fourier transforms have the form:

$$f(k, \theta, \phi) = \sum_{n=0}^{l} \frac{P_l^{(n)}(1)}{k^{n+1}} \times \begin{cases} (-1)^{\lfloor \frac{l-n}{2} \rfloor} \int_0^\infty r^{1-n} dr \sin(kr) f(r, \theta, \phi), & l+n \text{ is even} \\ (-1)^{\lfloor \frac{l-n+1}{2} \rfloor} \int_0^\infty r^{1-n} dr \cos(kr) f(r, \theta, \phi), & l+n \text{ is odd} \end{cases},$$

where [x] denotes the largest integer that does not exceed x, and $P_l^{(N)}$ is a series of Legendre polynomials.

* * * * *